(12) United States Patent
Dwivedi

(10) Patent No.: US 9,760,988 B2
(45) Date of Patent: Sep. 12, 2017

(54) MYOCARDIAL CLUSTERIFICATION AND ORIENTATION

(75) Inventor: Shekhar Dwivedi, Willoughby Hills, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 975 days.

(21) Appl. No.: 14/116,352

(22) PCT Filed: May 2, 2012

(86) PCT No.: PCT/IB2012/052183
§ 371 (c)(1),
(2), (4) Date: Nov. 8, 2013

(87) PCT Pub. No.: WO2012/153231
PCT Pub. Date: Nov. 15, 2012

(65) Prior Publication Data

US 2014/0081132 A1    Mar. 20, 2014

Related U.S. Application Data

(60) Provisional application No. 61/484,411, filed on May 10, 2011, provisional application No. 61/610,506, filed on Mar. 14, 2012.

(51) Int. Cl.
*A61B 6/00* (2006.01)
*G06T 7/00* (2017.01)
(Continued)

(52) U.S. Cl.
CPC ............ *G06T 7/0012* (2013.01); *A61B 6/037* (2013.01); *A61B 6/503* (2013.01); *A61B 6/507* (2013.01);
(Continued)

(58) Field of Classification Search
CPC ....... A61B 6/037; A61B 6/503; A61B 6/5217; A61B 6/5223
See application file for complete search history.

(56) References Cited

U.S. PATENT DOCUMENTS 5,431,161 A    7/1995 Ryals et al.
5,682,887 A    11/1997 Xu et al.
(Continued)

FOREIGN PATENT DOCUMENTS

CN    101650835    2/2010
WO    2005001769    1/2005

OTHER PUBLICATIONS

Cauvin, J. C., et al.; Automatic detection of the left ventricular myocardium long axis and center in thallium-201 single photon emission computed tomography; 1992; European Journal of Nuclear Medicine; 19(12)1032-1037.

(Continued)

*Primary Examiner* — Joseph M Santos Rodriguez

(57) ABSTRACT

A cardiac imaging method includes acquiring a projection image representation which includes a myocardium (S100). The myocardium is segmented and a mask is generated (S102). The mask is optimized (S104). A blood pool is determined from the optimized mask (S106) and the mask is skeletonized based on a clusterfication of the myocardial slices (S108). The center of mass is determined (S110) from the blood pool and the skeletonized mask. Myocardial parameters are determined (S112) from the skeletonized mask.

18 Claims, 25 Drawing Sheets

(51) Int. Cl.
    *A61B 6/03*      (2006.01)
    *G06T 7/11*      (2017.01)
(52) U.S. Cl.
    CPC .......... *A61B 6/5217* (2013.01); *A61B 6/5223* (2013.01); *G06T 7/11* (2017.01); *G06T 2207/10104* (2013.01); *G06T 2207/10108* (2013.01); *G06T 2207/20044* (2013.01)

(56) References Cited

U.S. PATENT DOCUMENTS

| | | |
|---|---|---|
| 6,065,475 A | 5/2000 | Qian et al. |
| 7,394,920 B2 | 7/2008 | Ficaro et al. |
| 2003/0069494 A1 | 4/2003 | Jolly |
| 2010/0232645 A1 | 9/2010 | Blaffert et al. |
| 2012/0321153 A1 | 12/2012 | Dwivedi et al. |

OTHER PUBLICATIONS

Germano, G., et al.; Automatic Quantification of Ejection Fraction from Gated Myocardial Perfusion SPECT; 1995; The Journal of Nuclear Medicine; 36(11)2138-2147.

"Pruning (morphology)"; Wikipedia; Apr. 11, 2011; http://en.wikipedia.org/w/index.php?title=Pruning_%28morphology%29&oldid=43532150.

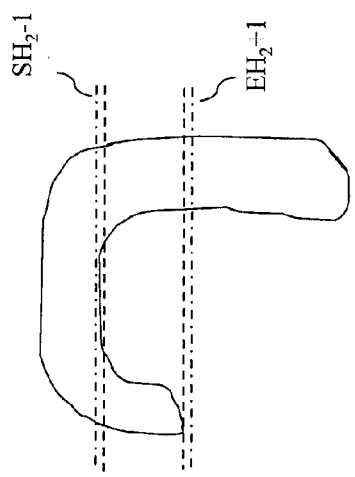
Figure 14A
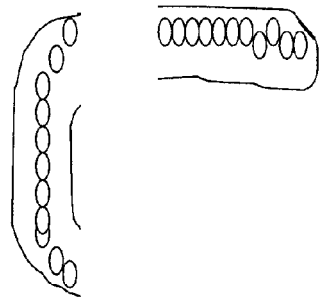
Figure 14E
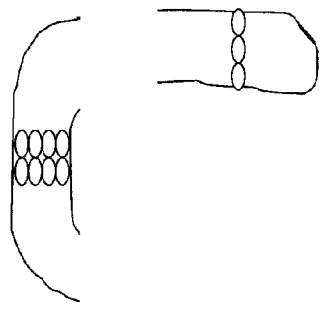
Figure 14D
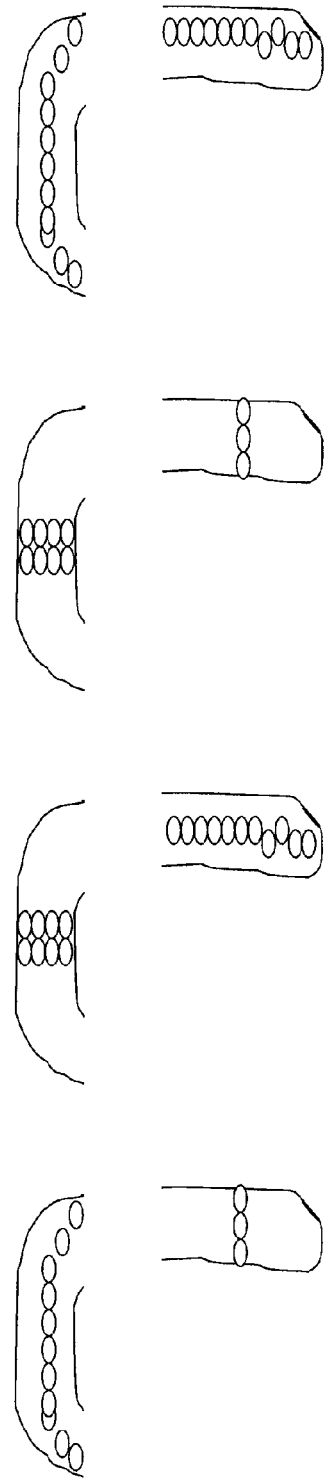
Figure 14C
Figure 14B

MYOCARDIAL CLUSTERIFICATION AND ORIENTATION

The present application relates to medical imaging arts. It finds particular application to region of interest (ROI) definition of myocardial tissue in diagnostic nuclear imaging.

In diagnostic nuclear imaging, a radionuclide distribution is studied as it passes through a patient's bloodstream for imaging the circulatory system or for imaging specific organs that accumulate the injected radiopharmaceutical. In single-photon emission computed tomography (SPECT), for example, one or more radiation detectors, commonly called gamma cameras, are used to detect the radiopharmaceutical via radiation emission caused by radioactive decay events. Typically, each gamma camera includes a radiation detector array and a collimator disposed in front of the radiation detector array. The collimator defines a linear or small-angle conical line of sight so that the detected radiation comprises projection data. If the gamma cameras are moved over a range of angular views, for example over a 180° or 360° angular range, then the resulting projection data can be reconstructed using filtered back-projection, expectation-maximization, or another image reconstruction technique into an image of the radiopharmaceutical distribution in the patient. Advantageously, the radiopharmaceutical can be designed to accumulate in selected tissues to provide preferential imaging of those selected tissues, such as cardiac tissue for the purpose of cardiac imaging.

In many cardiac SPECT studies, one of the most widely used diagnostic applications includes myocardial perfusion imaging where the left ventricle is of particular interest. Low intensities in SPECT images of the left ventricular (LV) area are related to perfusion defects typically due to coronary artery disease. The activity of the radiopharmacuetical in the LV area can be used to estimate parameters such as blood flow rate, flow reserve, ejection fraction, or other parameters relevant to diagnosis and treatment. To estimate these and other parameters, one wants to locate at a region of interest of at least the left ventricle and determine the geometry and orientation of the region of interest to accurately estimate parameters indicative of the patient's myocardial health. For a quantitative assessment of the myocardial parameters to be accurate depends, in part, on accurate and repeatable the determination of the myocardial geometry and orientation, more specifically left ventricle pose estimation.

The present application provides a new and improved method and system which overcomes the above-referenced problems and others.

In accordance with one aspect, a method for cardiac imaging is provided. Functional image data of a subject is acquired, which functional image data includes at least a myocardium. A pose and geometry of the myocardium are determined. Diagnostic parameters of the myocardium are estimated based on the determined pose and geometry.

In accordance with another aspect, the method further includes segmenting the left ventricle, generating a left ventricle myocardial mask, computing a center of mass of the left ventricle, skeletonizing the left ventricle myocardial mask to generate a myocardial skeleton, and pruning the myocardial skeleton.

In accordance with another aspect, a cardiac imaging apparatus is provided which includes a diagnostic scanner for generating functional imaging data of a subject from the diagnostic scanner, the functional imaging data including the myocardium, determining a pose and geometry of the myocardium, and estimating diagnostic parameters of the myocardium based on the determined pose and geometry. A display device displays at least the diagnostic parameters.

In accordance with another aspect, a cardiac imaging apparatus is provided which includes an acquiring unit which acquires functional image data of a subject, the functional image data including at least a myocardium. The determining unit determines a pose and geometry of the myocardium. An estimating unit estimates diagnostic parameters of the myocardium based on the determined pose and geometry.

One advantage relies in that myocardial pose computation accuracy and robustness is improved.

Another advantage relies in that accuracy of parameters based on the computed pose is improved.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 9B:
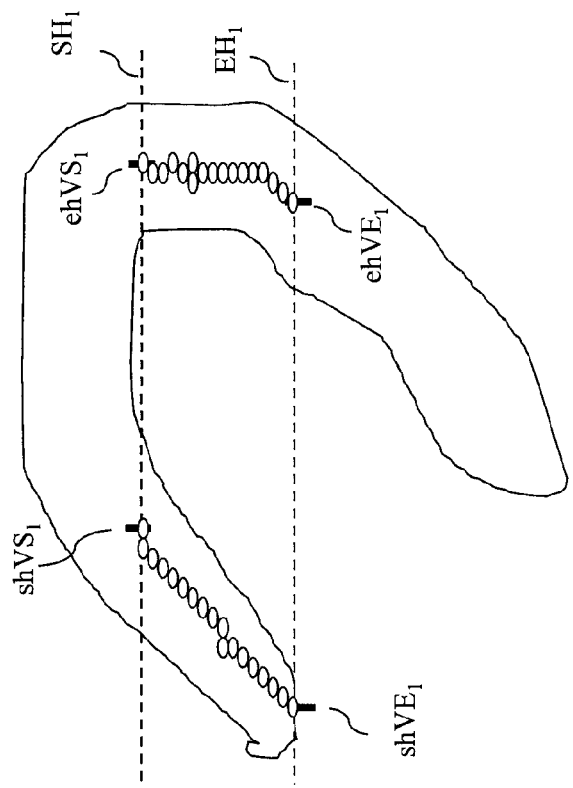
Figure 9A:
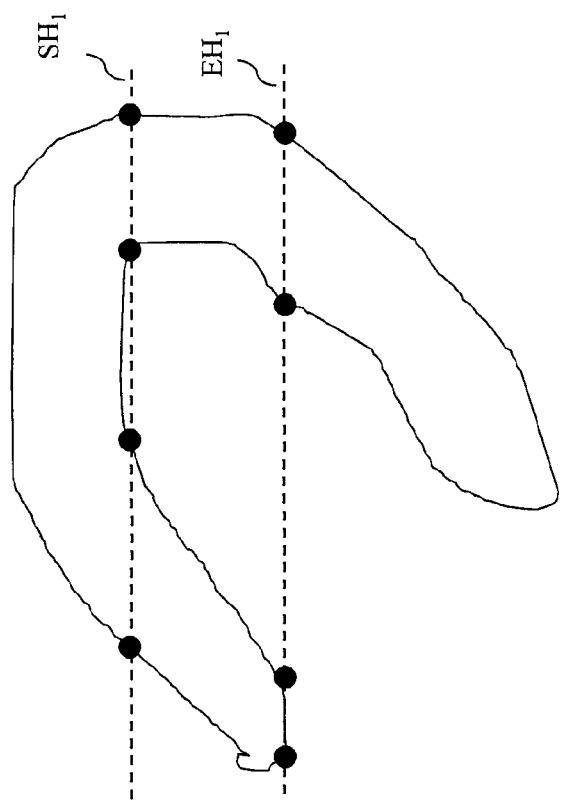
Figure 10B:
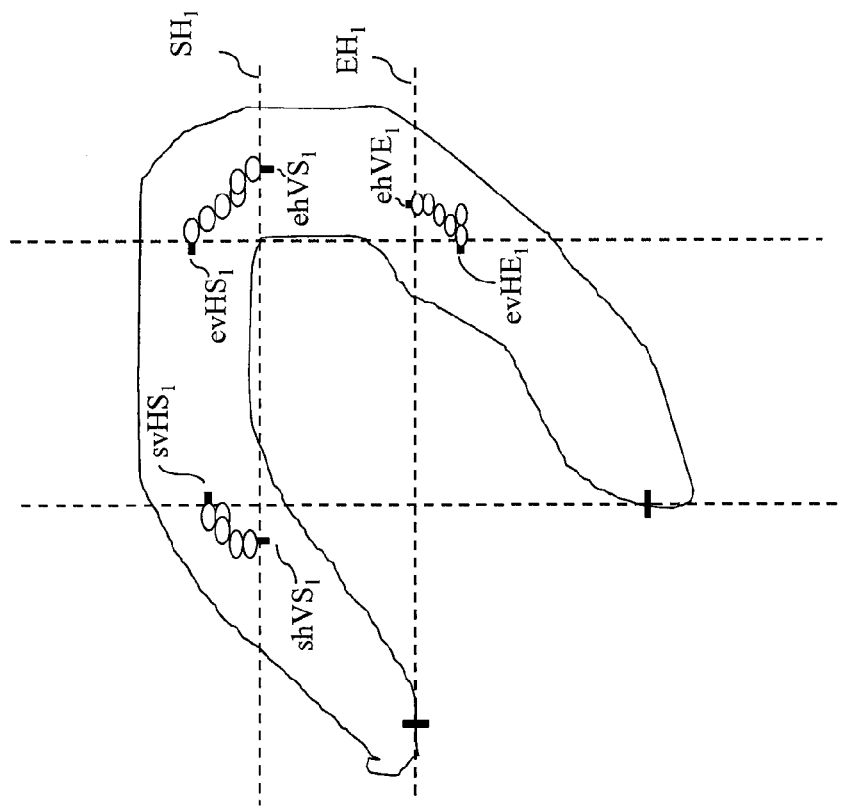
Figure 10A:
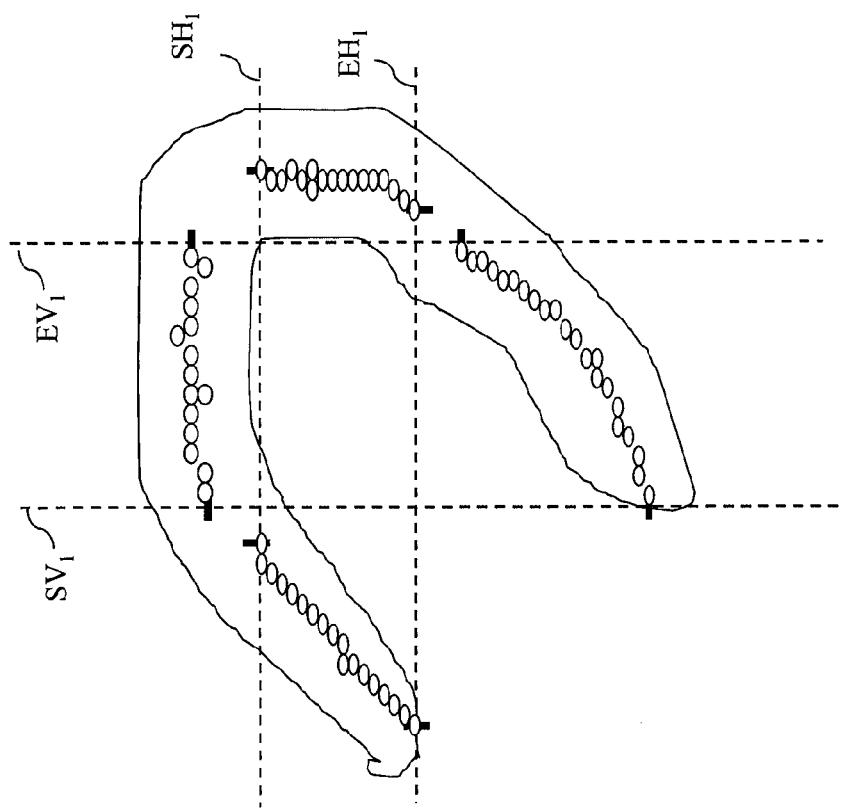
Figure 11A:
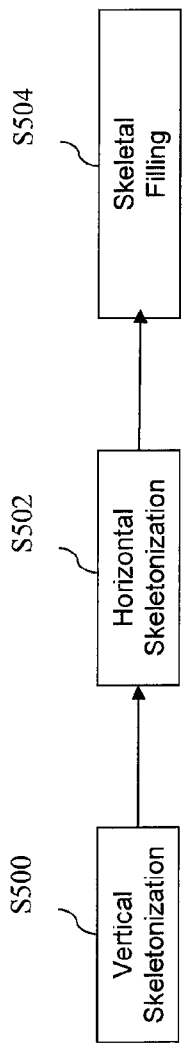
Figure 12B:
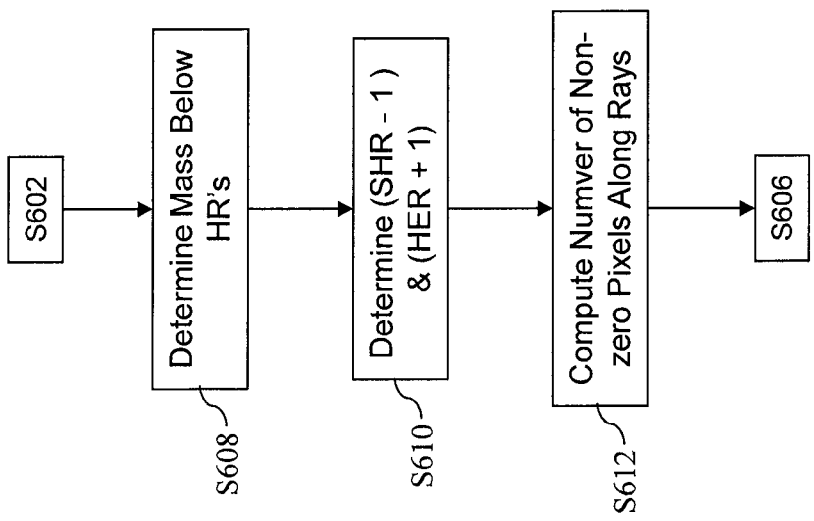
Figure 12A:
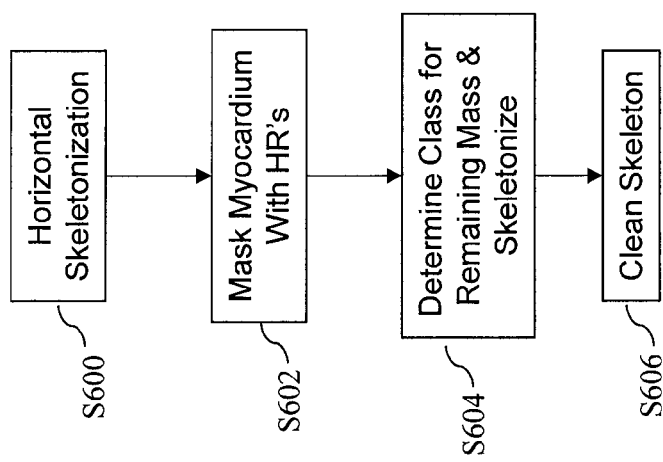
Figure 16:
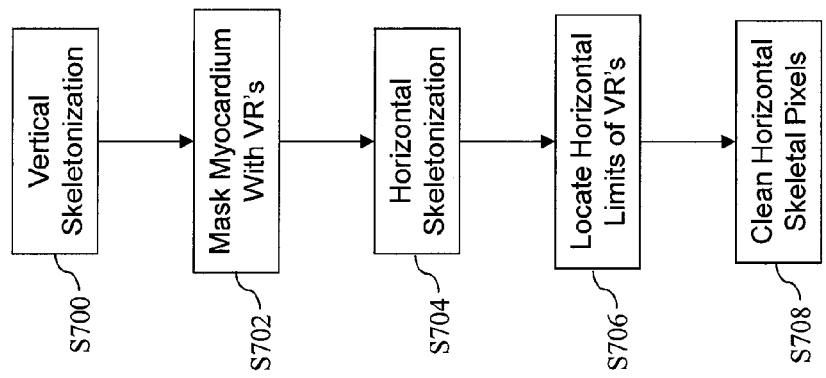
Figure 20:
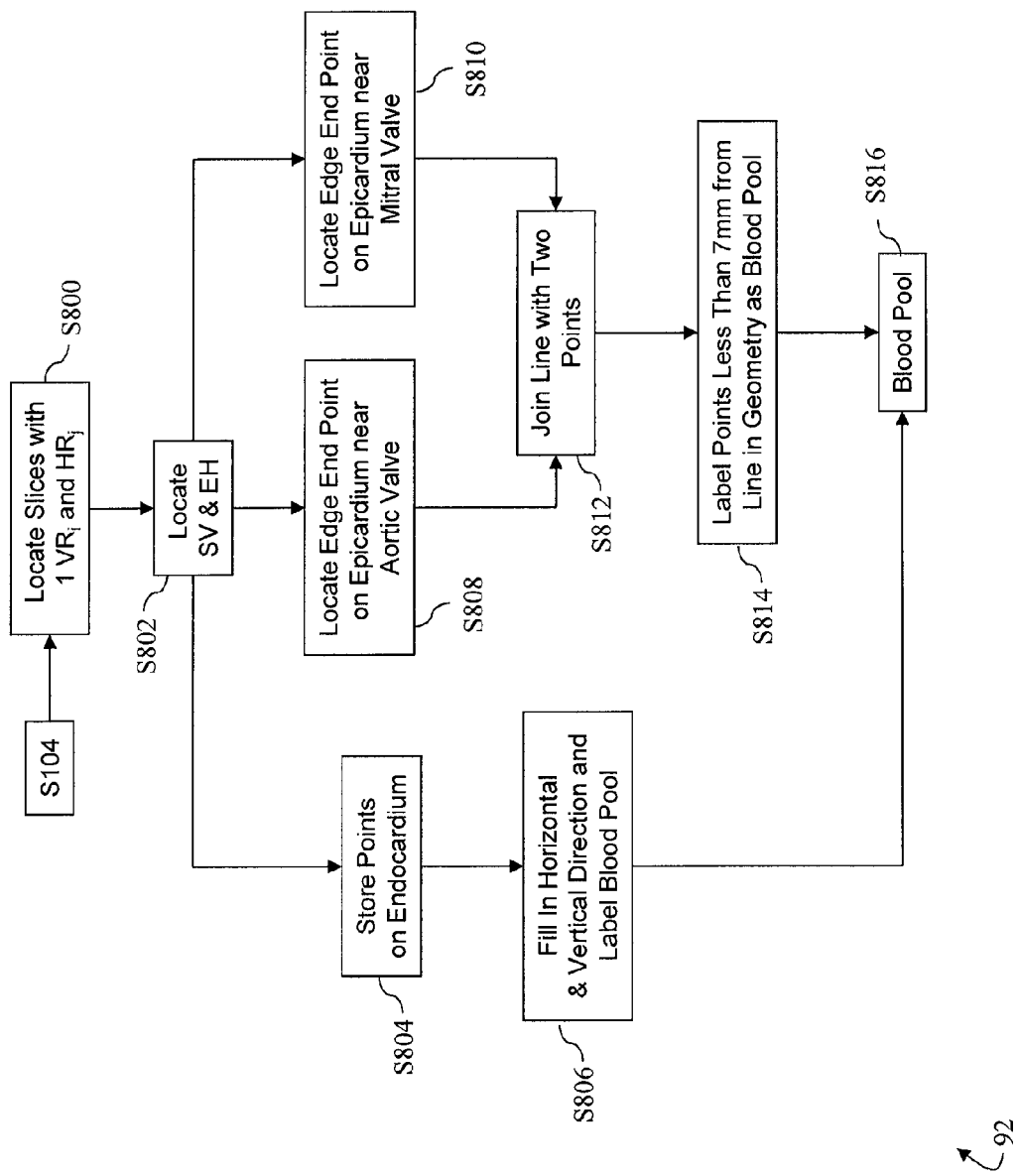
Figure 22B:
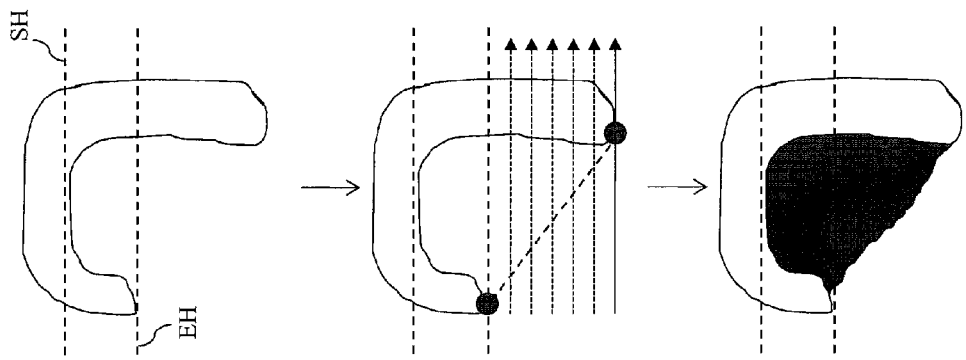
Figure 22A:
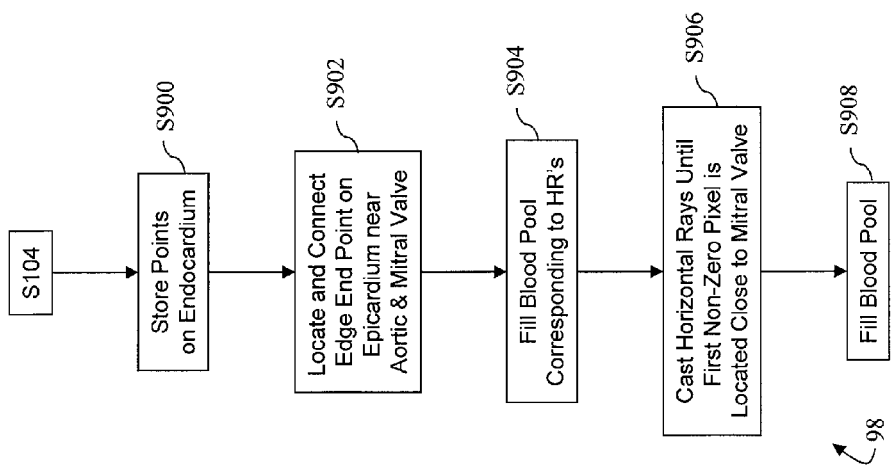
Figure 23A:
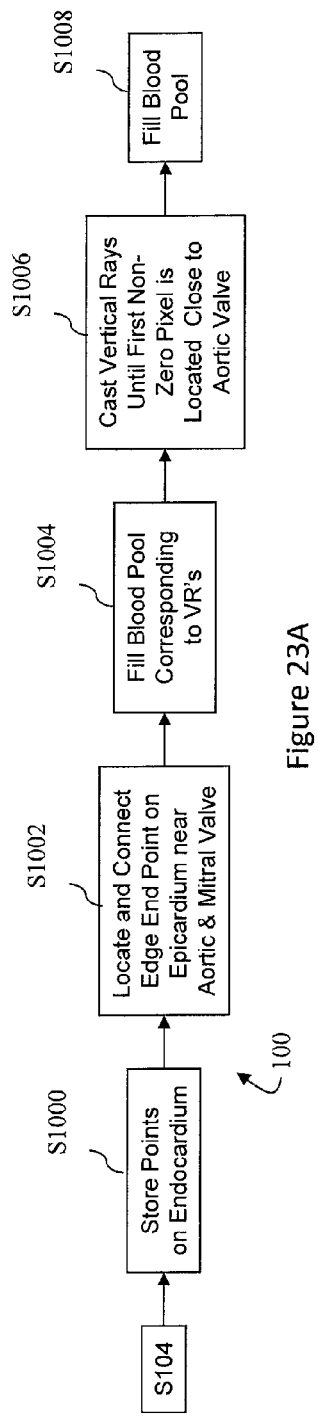
Figure 23B:
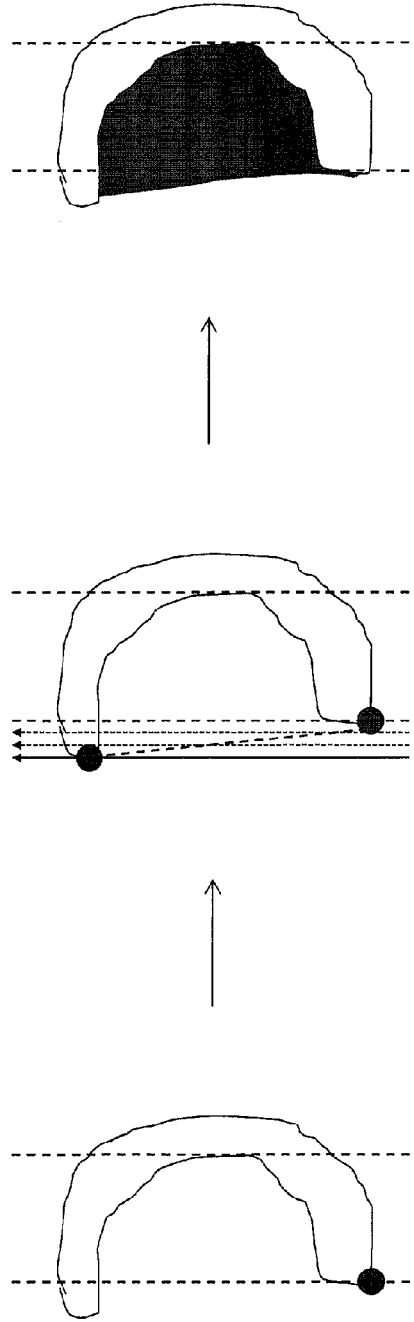
Figure 24:
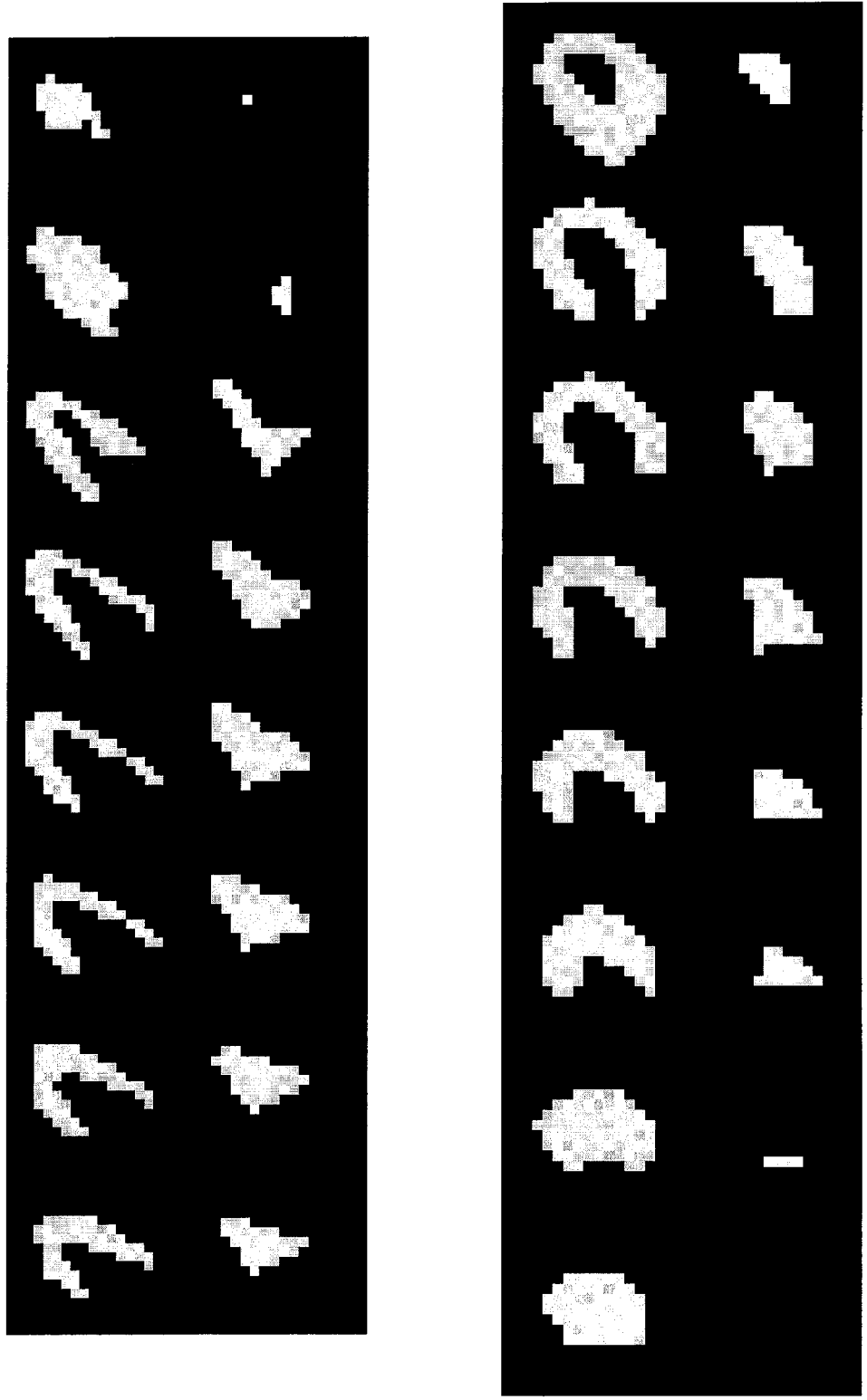
Figure 25:
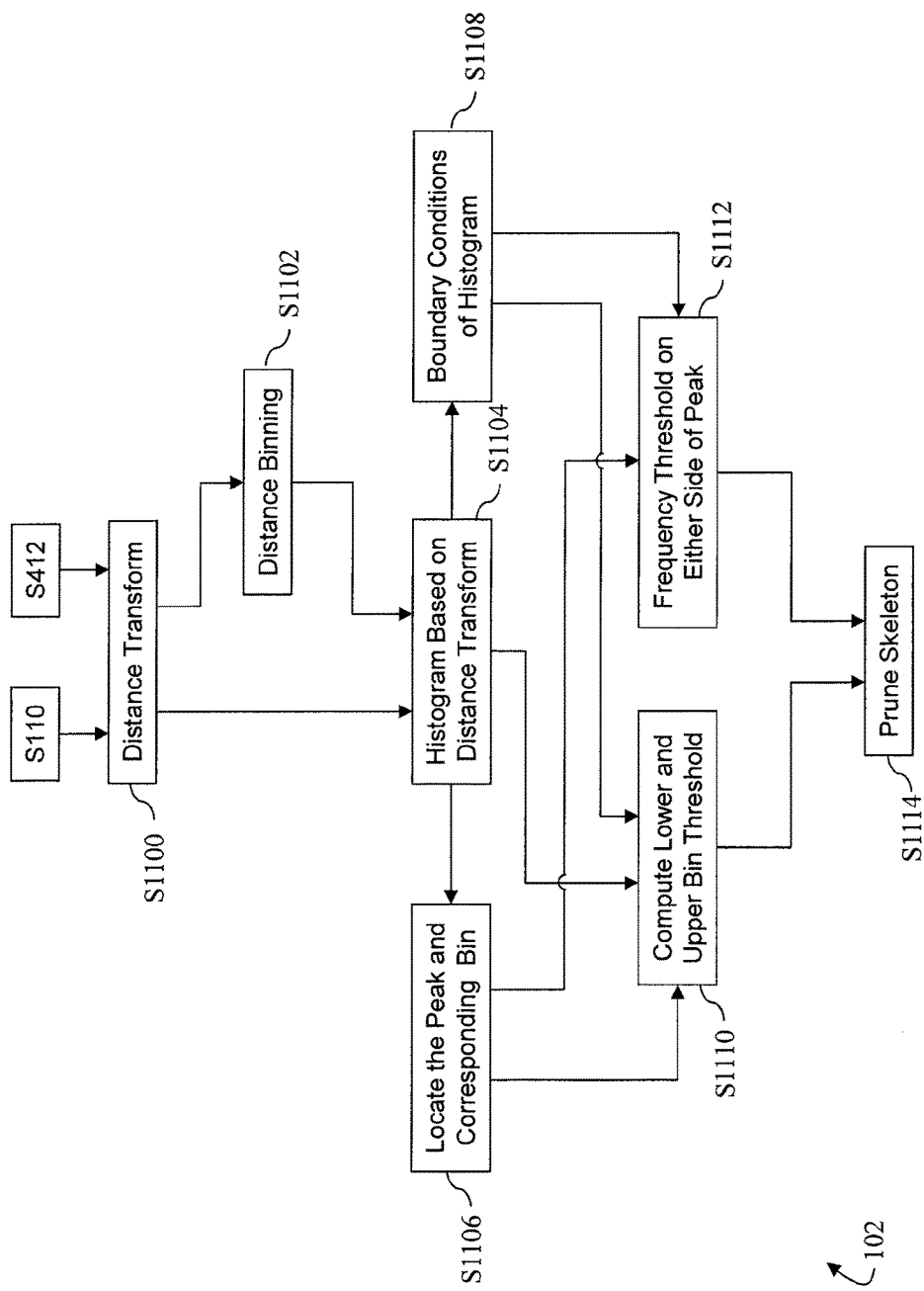

FIGS. 8A-8B, 9A-9B, 10A-10B, and 11B-11D illustrates a skeletonization method for a Type 1 myocardial cluster while FIG. 11A is a flow diagram representing the method for skeletonization method for a Type 1 myocardial cluster;

FIGS. 12A and 12B are flow diagrams representing a method for skeletonization method for a Type 2 myocardial cluster;

FIGS. 13A-13D, 14A-14E, and 15A-15D illustrate the skeletonization method for a Type 2 myocardial cluster;

FIG. 16 is a flow diagram representing a method for skeletonization method for a Type 3 myocardial cluster;

FIGS. 17A-17D and 18A-18B illustrate the skeletonization method for the Type 3 myocardial cluster;

FIGS. 19A-19E illustrated a skeletonization method for the Type 4 cluster;

FIG. 20 is a flow diagram representing a method for myocardial blood pool segmentation;

FIGS. 21A-21F illustrate the blood pool segmentation method;

FIG. 22A is a flow diagram representing another method for blood pool segmentation while FIG. 22B illustrates the blood pool segmentation method;

FIG. 23A is a flow diagram representing another method for blood pool segmentation while FIG. 23B illustrates the blood pool segmentation method;

FIG. 24 illustrates screen shots of binary masks and the corresponding blood pool from the various shape cluster types;

FIG. 25 is a flow diagram representing a skeletal pruning method; and

Figure 26:
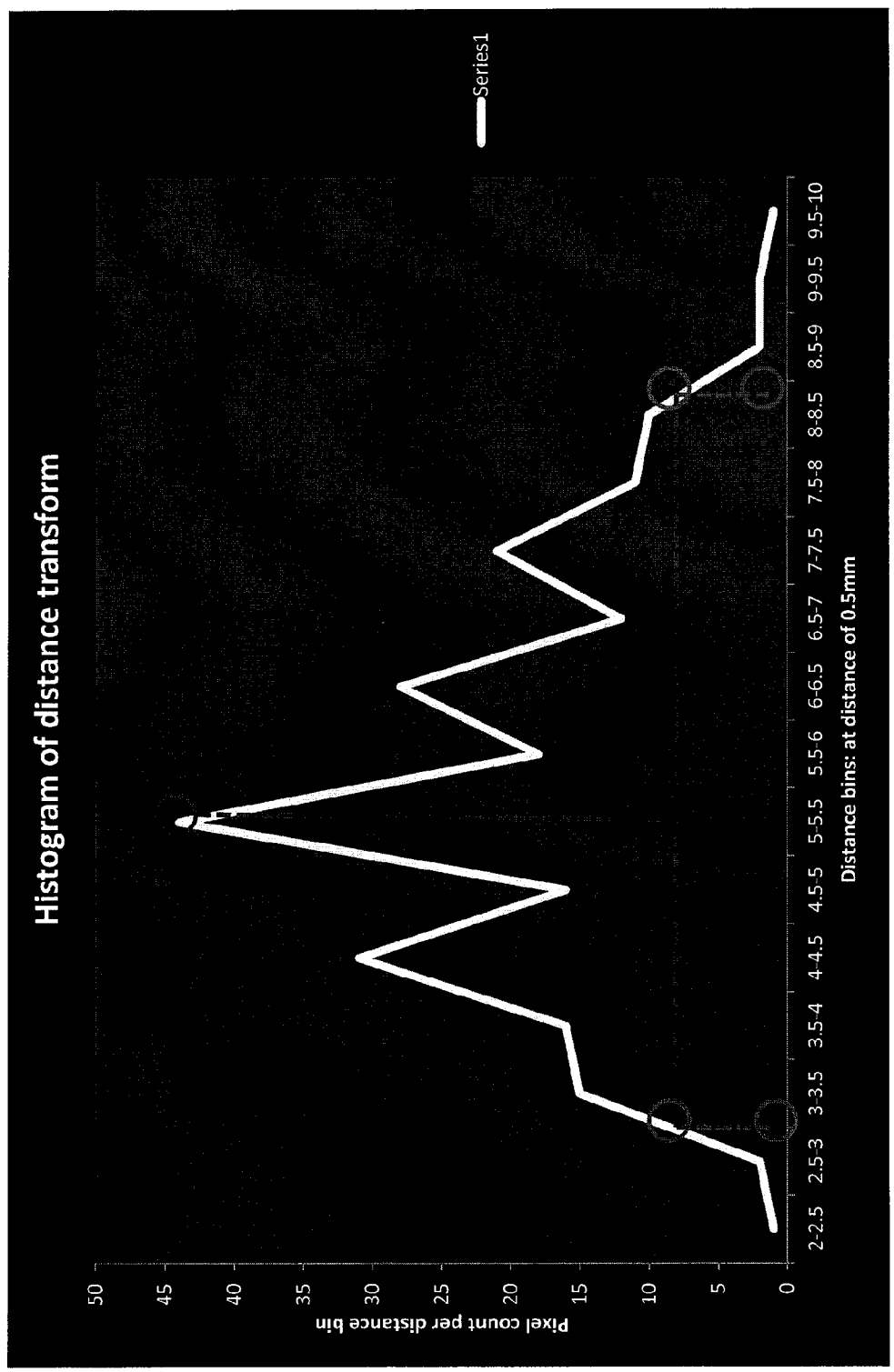

FIG. 26 illustrates a histogram for use in the skeletal pruning method.

Figure 1:
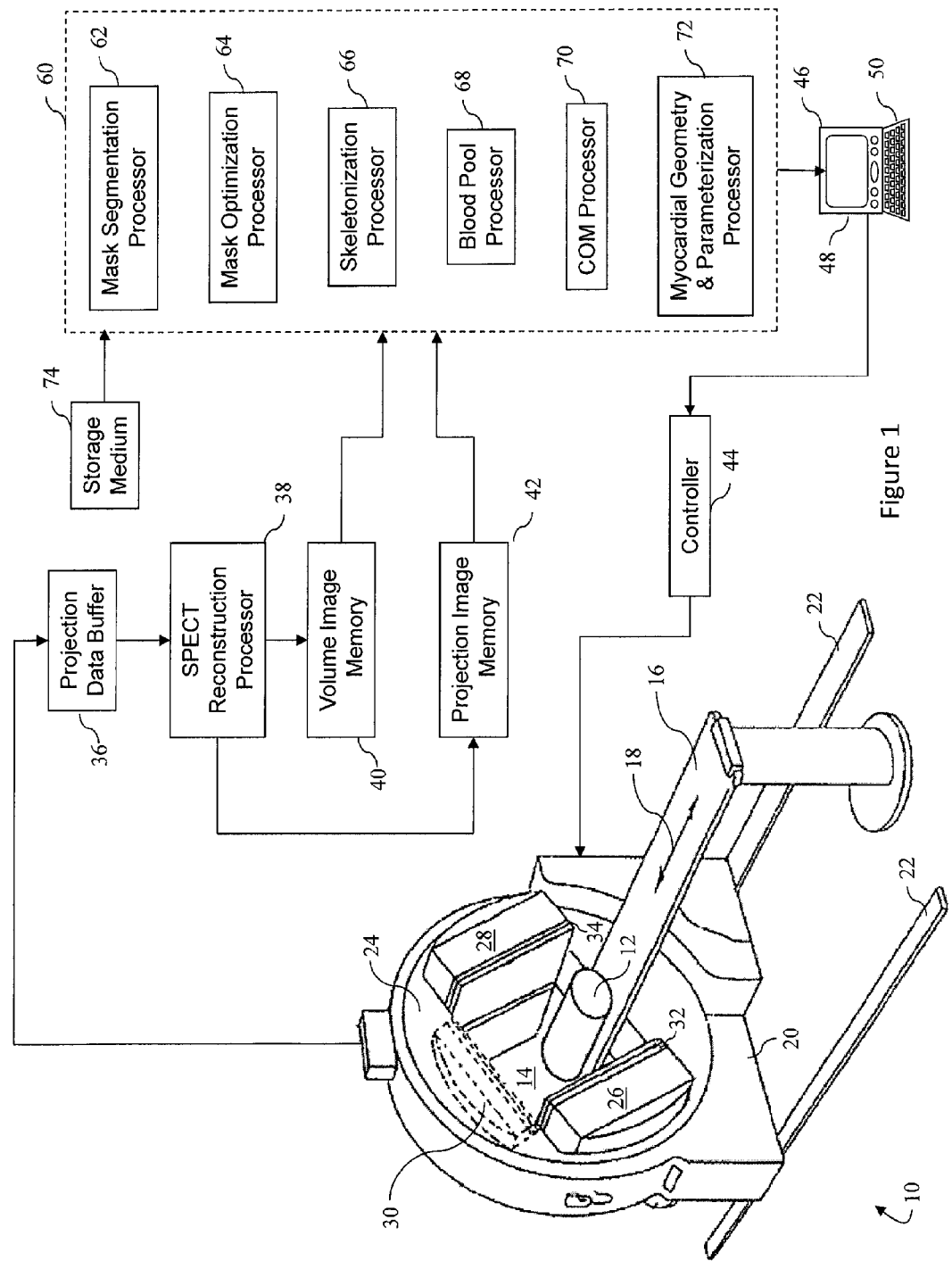
FIG. 1 is a diagrammatic illustration of a diagnostic imaging system with a processing unit programmed to perform myocardial clusterification based skeletonization and pose estimate.

With reference to FIG. 1, a diagnostic imaging system 10 acquires functional imaging data of a subject 12 within an examination region 14. Although a SPECT system is described, it is to be appreciated that other imaging modalities, such as positron emission tomography (PET) or the like are also contemplated. The diagnostic imaging system 10 includes a patient support 16 which is selectively translatable to facilitate positioning the subject 12 being imaged or examined at a desired location, e.g. so that the regions of interest are centered about a longitudinal axis 18. Alternatively, an outer gantry 20 is movably mounted on tracks 22 to achieve the desired position of the subject 12 relative to the imaging system 10 along the longitudinal axis 18.

An inner gantry 24 is rotatably mounted on the outer gantry 20 for stepped or continuous motion. The rotating inner gantry 24 defines the subject receiving examination region 14. One or more detector heads 26, 28, 30 are individually positionable on the rotatable inner gantry 24. The detector heads 26, 28, 30 rotate as a group about the examination region 14 and the subject 12 with the rotation of the rotatably inner gantry 24. The detector heads 26, 28, 30 are radially, circumferentially, and laterally adjustable to vary their distance from the subject 12 and spacing on the rotating gantry 24 to position the detector heads in any of a variety of angular orientations about a central axis.

The detector heads 26, 28, 30 each include an array of radiation detectors such as one of more scintillators that emit a flash of light or photons in response to incident radiation events from the radiopharmaceutical. The scintillator(s) are viewed by an array of photodetectors that receive the light flashes and converts them into electrical signals. Alternatively, an array of direct radiation to electrical pulse detectors is also contemplated. Suitable collimation is provided to define projection data, for example a radiation absorbing honeycomb collimator disposed in front of the detector array. A resolver circuit resolves the x, y-coordinates of each received radiation event and the energy of the incident radiation. The relative outputs of the photodetectors are processed and corrected in conventional fashion to generate an output signal indicative of: (i) a position coordinate on the detector head at which each radiation event is received, (ii) an energy of each event, and (iii) an angular position of the detector head. The energy is used to differentiate between various types of radiation such as multiple emission radiation sources, stray and secondary emission radiation, scattered radiation, transmission radiation, and to eliminate noise.

In SPECT imaging, a projection image representation is defined by the radiation data received at each coordinate on the detector head. In SPECT imaging, a collimator defines the rays along which radiation is received. It should be appreciated that although the illustrated embodiment is described with regard to SPECT imaging, other nuclear imaging modalities are also contemplated, such as positron emission tomography (PET) imaging systems.

In PET imaging, the detector head outputs are monitored for coincident radiation events on two heads. From the position and orientation of the heads and the location on the faces at which the coincident radiation is received, a ray between the coincident event detection points is calculated. This ray defines a line along which the radiation event occurred. In both PET and SPECT, the projection data from a multiplicity of angular orientations is stored in a projection data buffer 36, and then reconstructed by a reconstruction processor 38 into a transverse volumetric image representation and a projection image representation of the region of interest, which is stored in a volume image memory 40 and a projection image memory 42, respectively. The projection image representation can be a two-dimensional (2D) axial representation of a volume in which the highest attenuation voxels along lines projected through the volume data set are selected. With volumetric image representations, 3D spatial relationships are preserved at the cost of computation time and visualization of smaller features versus projection image representations. Both image representations may include a plurality of transverse slices of image representations along the longitudinal axis 18. The functional imaging system 10 is operated by a controller 44 to perform selected imaging sequences of a selected target area of the subject. A console 46 includes a display unit 48 which displays a graphic user interface (GUI) which a clinician can use with a user input device 50 for controlling the scanner controller 44 to select scanning sequences or protocols.

Figure 2:
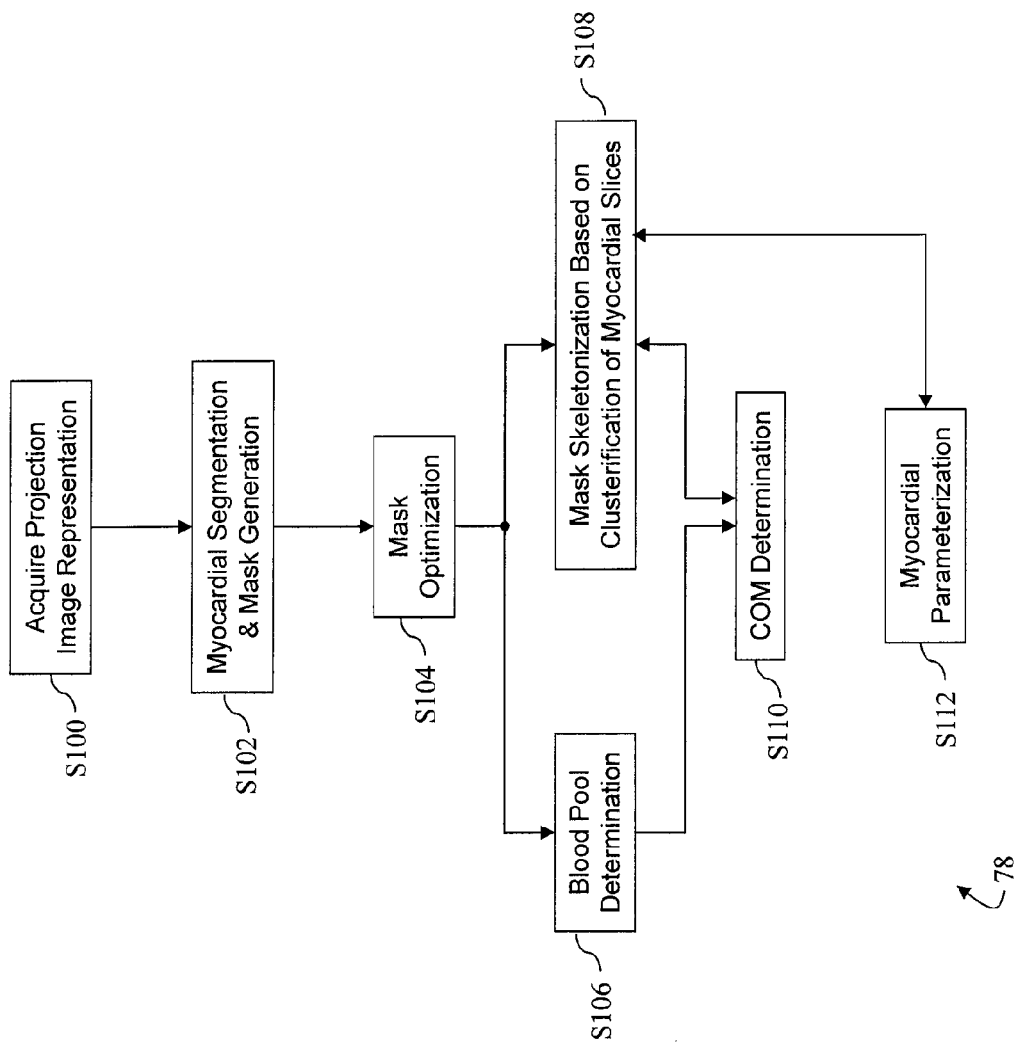
FIG. 2 is a flow diagram representing a method for determining myocardial parameters.

With reference to FIGS. 1 and 2, the system 10 includes a processing unit 60 which includes several processors which perform algorithms for myocardial segmentation 62, myocardial mask optimization 64, myocardial mask skeletonization and pruning 66, Blood pool determination 68, Center-of-Mass (COM) determination 70, and parameterization 72. The processing unit 60 is coupled to a computer readable storage unit 74 that stores received image data, processed image data, algorithms for determining for processing, generating, reconstructing etc., algorithms for determining myocardial segmentation, myocardial mask correction, COM determination, myocardial mask skeletonization, skeletal pruning, and the like. It is to be appreciated that the projection data buffer 36, volume image memory 40, projection image memory 42, and storage medium 74 may be part of a single computer readable memory module or implemented as separate modules.

The processing unit 60, with the various processors 62, 64, 66, 68, 70, 72, performs a pose estimate algorithm 78 which accounts for the myocardial shape, geometry, endocardium, epicardium, and proximity to other organs. The skeletonization algorithm is based on clusterification of transverse myocardial slices, exploiting the thickness slicewise and then combining each 2D skeleton into a 3D skeleton. The center-of-mass computation adapts blood pool segmentation for determining the x,y-direction COM for each slice and the 3D skeleton for determining the z-direction COM.

After the reconstructed projection volume is acquired S100 with the system 10, the myocardial segmentation processor 62 receives the reconstructed volume representation (and/or projection image representations) stored in the volume image memory 40 and analyzes each slice of the volume to define a location and boundary of a three-dimensional (3D) region of interest (ROI) of the myocardium without requiring the aid of an anatomical image or a human operator, such as described in U.S. Application 61/311,406. Once the ROI is determined, a 3D binary mask is generated of the corresponding ROI S102. The binary mask can be super-positioned on either a projection and/or the volumetric image representation and can be provided to the display unit 48 for viewing by a clinician.

The myocardial mask optimization processor 64 receives the determined myocardial masks from the segmentation processor 62 and corrects the mask for defects or deviations S104. Deviations in the myocardial mask, especially in transverse volumes, resulting from over- and under-perfusion can lead to significant errors in the parameters determined by the parameterization processor 72.

The skeletonization processor 66 receives the optimized myocardial masks from the optimization processor 64 and determines a skeleton for myocardial tissue of each optimized mask based on a clusterification based skeletonization algorithm. The clusterification based skeletonization algorithm sorts the optimized masks into various shape clusters. Then a 2D skeletonization method adapted to each cluster type is performed. The 2D skeletons are composited into a 3D stack which is then optimized with a distance binning and pruning algorithm that uses the COM determined from the blood pool segmentation processor 68. The blood pool determination and segmentation processor 68 receives the optimized myocardial mask from the optimization processor 64 and determines designates the pixels within the endocardium of a myocardial cavity as blood pool pixels.

The COM processor 70 receives the segmented blood pool mask from the blood pool processor 68 and determines the x and y coordinates of the COM based on centroid of each blood pool. The z coordinate of the COM is computed based on the extents of the myocardial mask in the z direction. The skeletonization processor 66 uses the blood pool's COM's for the pruning algorithm to prune or remove extraneous skeletal pixels which can affect a subsequent ellipsoid fitting. The COM processor 68 fits an ellipsoid to the optimized skeleton from which the pose, e.g. azimuth angle, elevation angle, and the like, can be estimated.

A geometry and parameterization processor 72 determines the myocardial geometrical estimates, such as cardiac azimuth, elevation angles, and the like, from the fitted ellipsoid and determines quantifiable parameters based on the ROI, mask, blood pool, skeleton and/or ellipsoid and the determined myocardial geometrical estimates. Quantifiable parameters includes, in the context of cardiac assessment, myocardial blood flow, regional myocardial blood flow, flow reserve, ejection fraction, and the like. It should be appreciated that the parameters tailored for a specific imaging study, such as cardiac imaging, pulmonary imaging, cerebral imaging, or the like, are also contemplated.

In cardiac imaging and parameterization, the left ventricle is of particular interest. The following algorithms will be described in reference to left ventricle (L.V) imaging. For example, the processors 62, 64, 66, 68, 70 of the processing unit 60 can perform L.V. segmentation, L.V. mask optimization, L.V. mask skeletonization, L.V. blood pool determination, and L.V center-of-mass determination, respectively. Furthermore, the parameterization processor 72 determines several parameters, e.g. blood flow, flow reserve, ejection fraction, and the like, of the L.V. It should be appreciated that the processing unit 60 can perform the following algorithms to various structures of the cardiac region.

The mask optimization processor 64 optimizes the myocardial masks for two extereme cases: over-segmentation in which the myocardial tissue is heavily over-perfused and under-segmentation in which the myocardial tissue is heavily under-perfused. The top and bottom ends of the L.V. transverse volume are important for ellipsoid fitting and L.V. angle determination, which will be discussed later. An inaccuracy in the L.V. angle can significantly effect the parameters determined by the parameterization processor 60.

Figure 3:
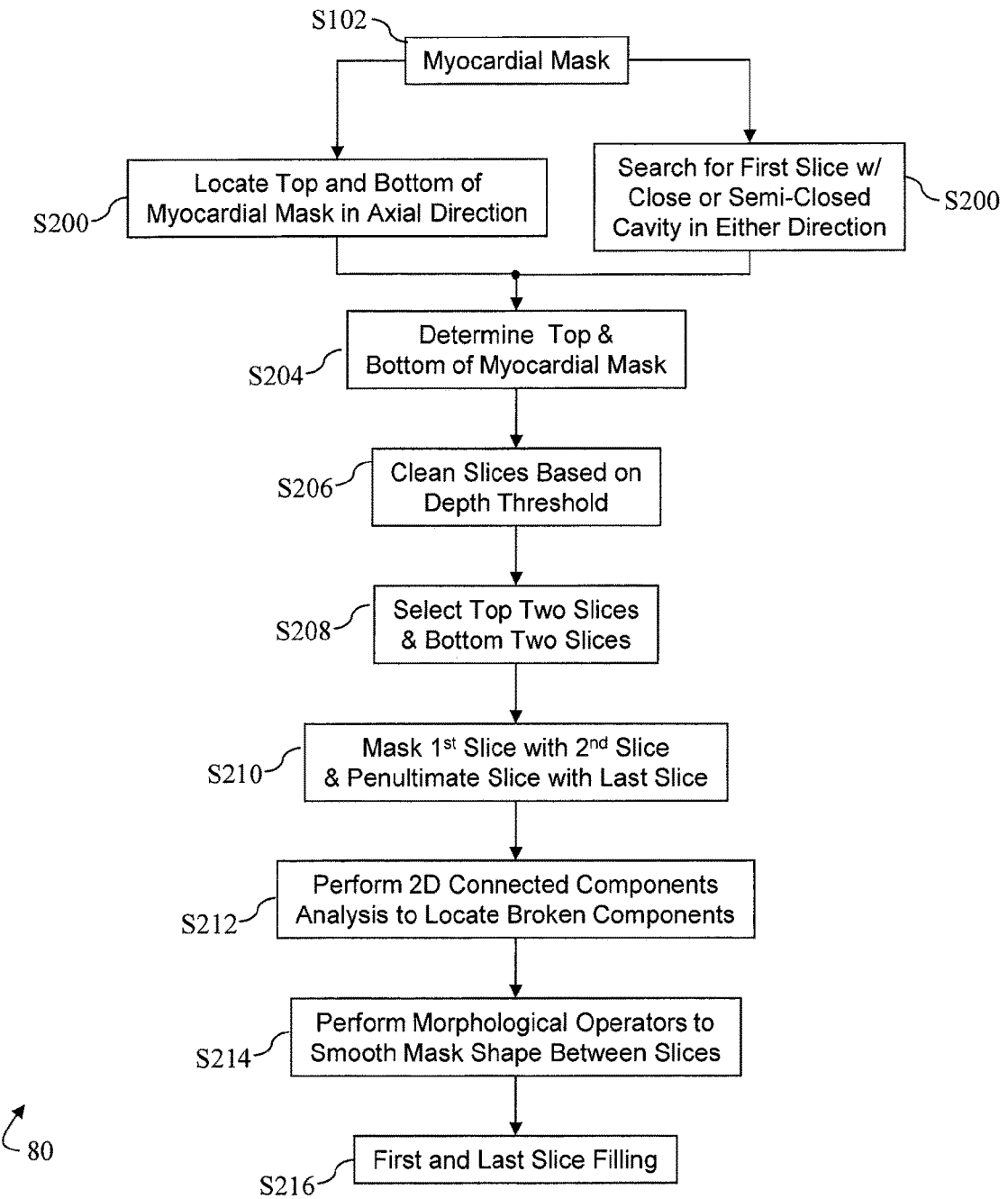
FIG. 3 is a flow diagram representing a method for myocardial masking and mask optimization.

With reference to FIG. 3, an algorithm 80 for correcting the binary masks that suffer from over-segmentation is presented to prune the unnecessary thickness at the top and bottom of the L.V. transverse volume and then to properly shape top and bottom slices. After the L.V. volume is segmented and the corresponding binary masks are generated S102, then the first slice and the last slice with closed or semi-closed cavity are located S200 along with first and last slice with no cavity S202 which will be adjacent to the slice from step S200. Once the location of these four slices is determined, the depth at the top and the bottom of the L.V mask is determined S204. The depth at any end refers to stacking up of lices with no cavity apart from one coming from S202. The slices of the L.V. cavity is then optimized or cleaned S206 by removing unnecessary slices beyond the four slices determined in S200 and S202. The number of slices "cleaned" is determined according to a preselected threshold value. When the L.V. is over-perfused (resulting in over-segmentation), the first slice (without the cavity) may have more or extraneous pixels than the next slice (with the cavity). The same situation can occur with the last slice and the penultimate slice. In these situations the myocardial masks of the first and last slice are optimized to alter the shape of the mask to closely match of the shape of the second slice and the penultimate slice, respectively. After the top two slices and last two slices are selected S208, then the first slice (without the cavity) is masked with the second (slice with the cavity) and similarly the last slice (without the cavity) is masked with the penultimate slice (with the cavity) S210. A 2D connected components analysis S212 is performed on both sets to locate broken components at the top and bottom of the L.V. volume. If broken components are located, the optimization of the first and last masks is not correct. Morphological operations, such as pruning, are performed S214 on the first and last slices such that the first slice closely matches the shape of the second slice and the last slice closely matches the shape of the penultimate slice.

Figure 4:
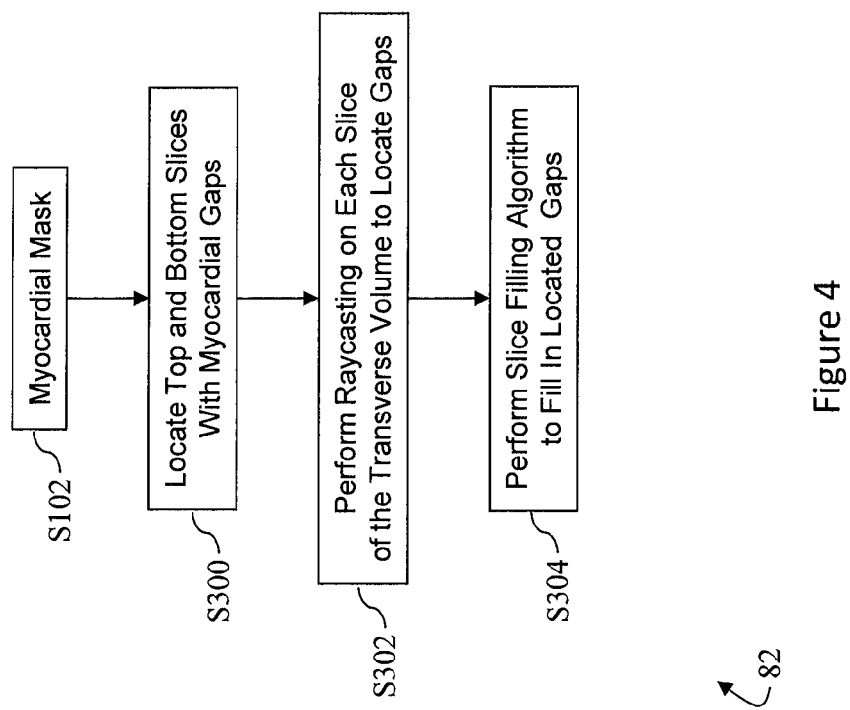
FIG. 4 is another flow diagram representing a method for myocardial mask optimization.

With reference to FIG. 4, an algorithm 82 for correcting the binary masks that suffer from under-segmentation is presented to fill in gaps where portions of the myocardium of the L.V. are missing due to under-perfusion. The top and bottom slices of the L.V. transverse volume are located S300 and binary ray casting is performed on each slice S302 to located gaps. If gaps are located in the selected slices, a slice filling algorithm is performed S304 to fill in the located myocardial gaps. The steps 302 and S304 are repeated for the next two intermediate slices of the L.V. volume until a common point is reached. For example, if there are 25 slices in the L.V. transverse volume, then steps 302 and S304 are repeated 13 times.

After the over-segmentation algorithm 80 and under-segmentation algorithm 82 are completed, the result is a balanced myocardial mask at the top and the bottom while addressing issues such as filling the myocardial gaps for the cases that are under-perfused.

Figure 5:
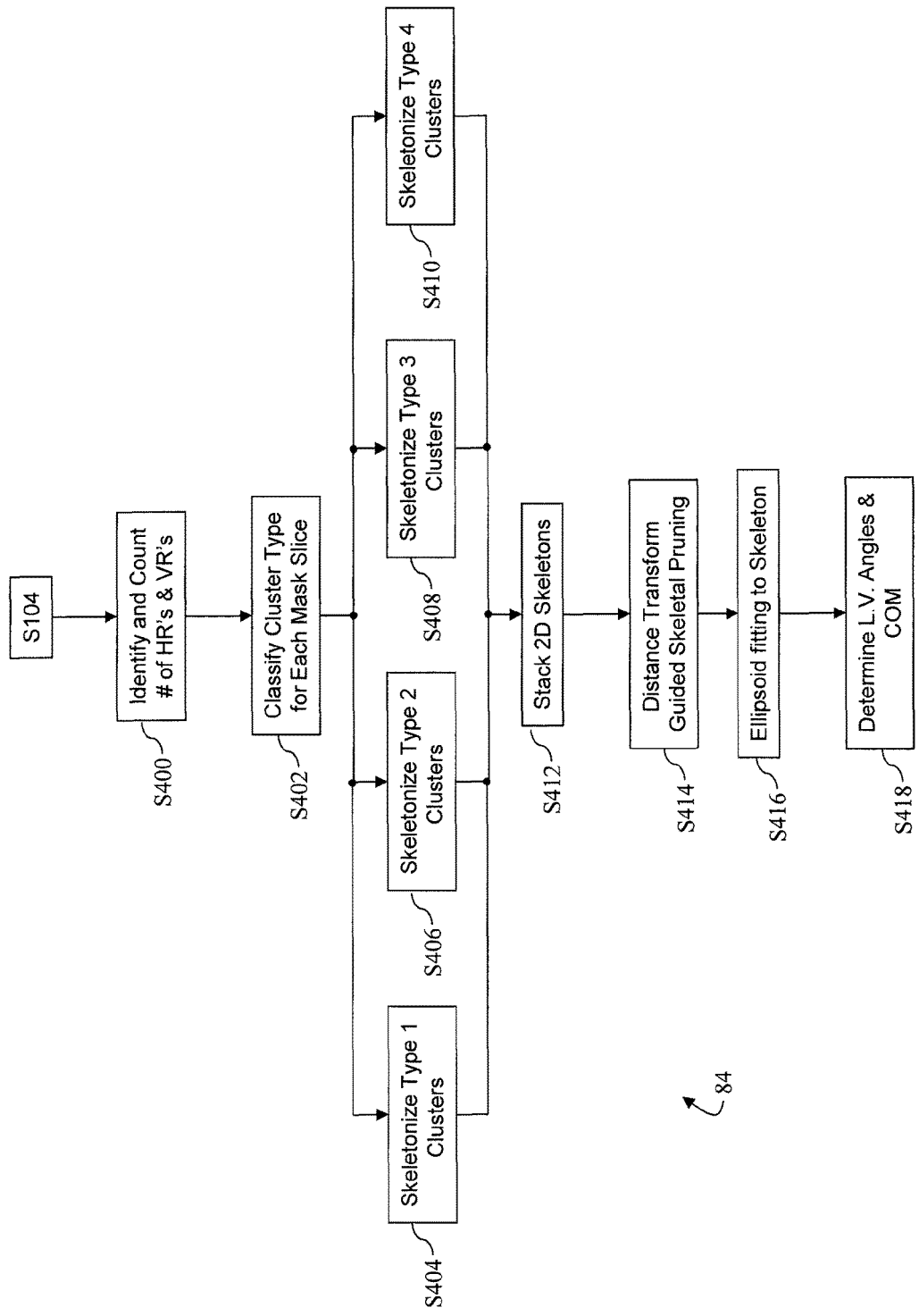
FIG. 5 is a flow diagram representing a method for myocardial clusterification based skeletonization and pose computation.
Figure 6:
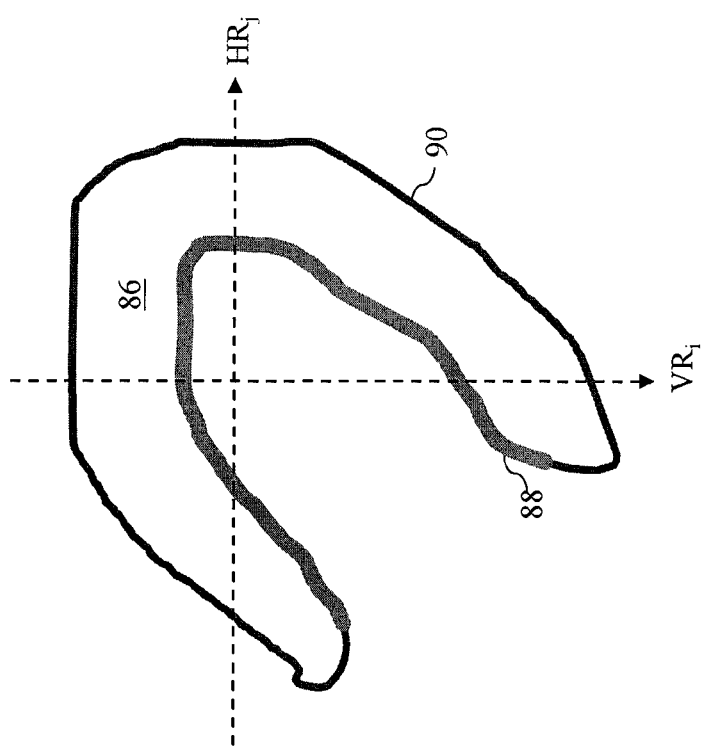
FIG. 6 illustrates various anatomical structures of myocardial tissue, more specifically the left ventricle.
Figure 7A:
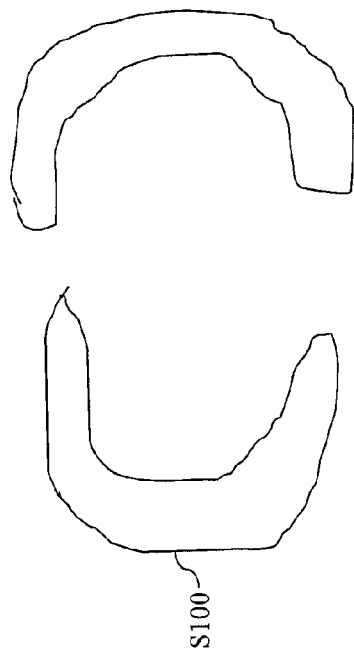
FIG. 7A-7D illustrates various types of myocardial shape clusters.
Figure 7D:
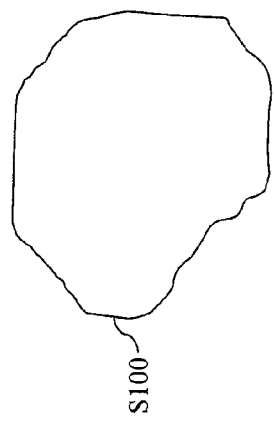
Figure 7C:
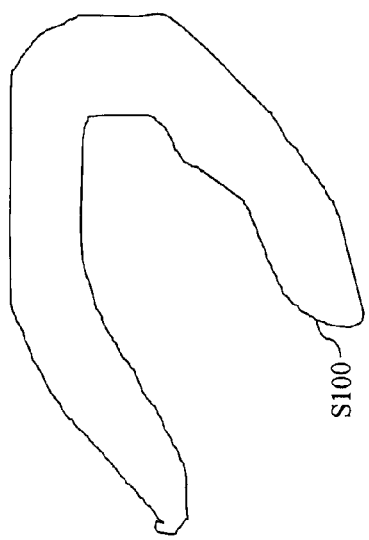
Figure 7B:
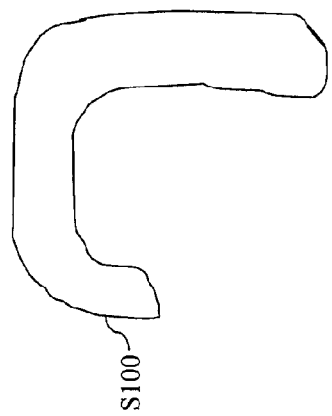

With reference to FIGS. 5 and 6, the skeletonization processor 66 generates a skeleton for each optimized binary mask of the L.V. transverse volume with a cluster based skeletonization algorithm 84. Cardiac angles, such as azimuth and elevation angle, are determined based on ellipsoid fitting of the skeleton. Skeletonization process and its accuracy is critical for angle generation. The skeletonization algorithm 84 is based on clusterification of the myocardial mask slices in 2D. The algorithm 84 exploits the geometry of the myocardium 86 and adjoining organs, the epicardium 88 and endocardium 90, in generating the skeleton. Each slice is assigned an appropriate cluster type S402 based on the number of horizontal rays ($HR_j$) and vertical rays ($VR_i$) S400 in the slice and then each cluster type is sorted then skeletonized S404, S406, S408, S410 accordingly. The 2D skeletons are stacked S412 to form a 3D skeleton which is then pruned S414 to remove any extraneous pixels at the boundaries. An ellipsoid is then fitted S416 to the pruned skeleton from which the L.V. angles, azimuth and elevation, and COM in the z-direction are determined S418.

The $VR_i$ and $HR_j$ are defined based on ray hits in their respective directions. According to equation 1, a pixel (i,j) is a ray hit $RH_{i,j}$ if it is a foreground pixel (F) and one of its connecting pixels is a background pixels (B).

$$RH_{i,j} = \begin{cases} \text{true}, & \bigcap_{i,j}(i,j) \in F, \bigcup_{\substack{i-1 \leq a \leq i+1 \\ j-1 \leq b \leq j+1}} [(a,b) \in B] \\ \text{false}, & \text{otherwise} \end{cases} \quad \text{equation (1)}$$

Equations 2 and 3 define $VR_i$ and $HR_j$ as being a vertical ray which intersects at least 4 non-zero pixels in a row and a horizontal ray which intersects at least 4 non-zero pixels in a column, respectively.

$$VR_i = \begin{cases} \text{true}, & 4 \leq \sum_{j=0}^{columns} RH_{i,j} \\ \text{false}, & \text{otherwise} \end{cases} \quad \text{equation (2)}$$

$$HR_j = \begin{cases} \text{true}, & 4 \leq \sum_{i=0}^{rows} RH_{i,j} \\ \text{false}, & \text{otherwise} \end{cases} \quad \text{equation (3)}$$

With reference to FIGS. 7A-7D, the myocardial shape clusters are defined and sorted into Type 1 (FIG. 7A), Type 2 (FIG. 7B), Type 3 (FIG. 7C), and Type 4 (FIG. 7D) so that the skeletonization process is tuned to each incoming type of myocardial mask shape. In this manner, clusterification of slice along with shape information ensures that cases with or without shape defects are handled accurately.

Figure 8B:
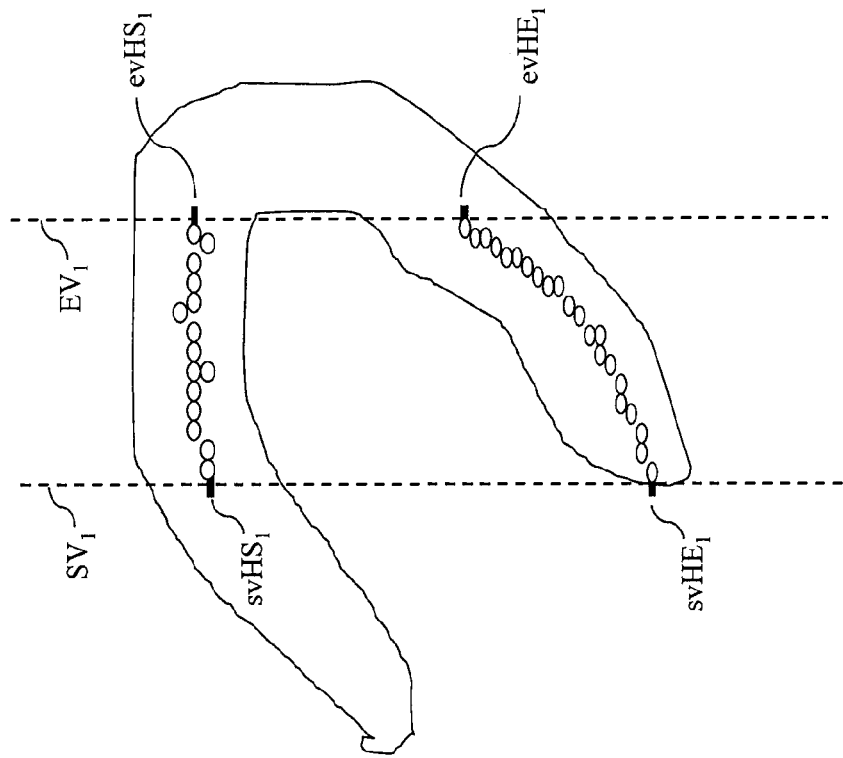
Figure 8A:
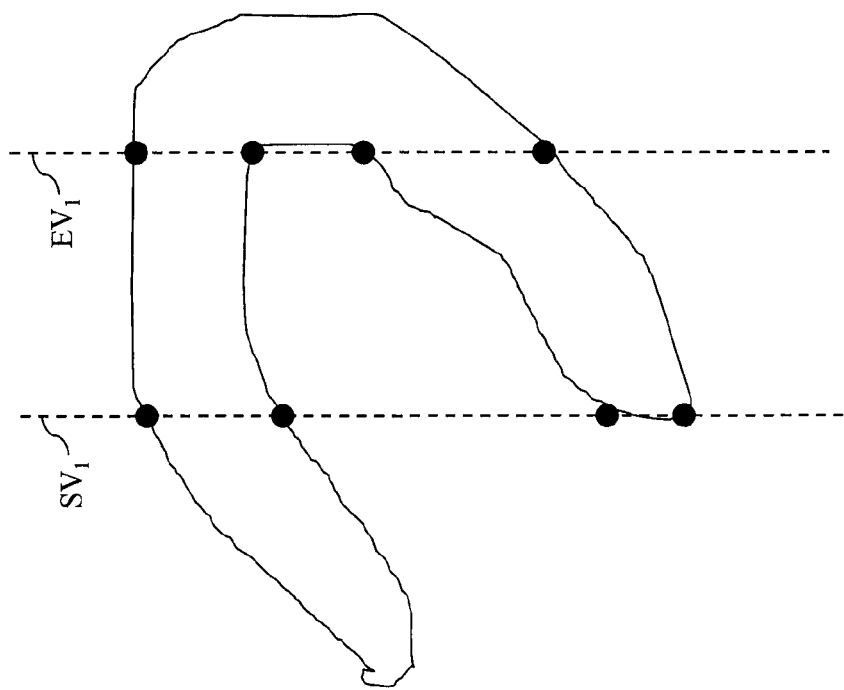

With reference to FIGS. 8A and 8B, Type 1 Clusters are defined as having both $VR_i$'s and $HR_j$'s, i.e. $VR_i>0$ and $HR_j>0$. To determine the skeleton for Type 1 Clusters S404 both vertical skeletonization and horizontal skeletonization is performed. For vertical skeletonization, vertical rays $VR_i$ are casted and the ray hits $RH_{i,j}$ are recorded according to equations 4:

$$PVR_i = \bigcup_{j=0}^{columns} (j|VR_i|RH_{i,j}) \quad \text{equation (4)}$$

where $PVR_i$ is a set of ray hits on ray $VR_i$. From the ray hits $PVR_i$, the skeletal pixels $SVR_i$ are determined according to equation 5:

$$SVR_i = \bigcup_{a=0}^{1} \left\{ \frac{PVR_{i,2a+1} + PVR_{i,2a+2}}{2} \middle| i, \frac{PVR_{i,2a+1} + PVR_{i,2a+2}}{2} \in F \right\} \quad \text{equation (5)}$$

and $SVR_i$ represents the pixel locations of the skeleton along ray $VR_i$. Each skeletal pixel is equidistant between two corresponding hits on a vertical ray. Once the skeletal pixels are obtained, the start vertrical ray $SV_1$ and end vertical ray $EV_1$ are defined as the first and last $VR_i$'s according to equation 6:

$$\{SV_1, EV_1\} = \left\{ \min_{1 \leq i \leq columns} \{i | VR_i\}, \max_{1 \leq i \leq columns} \{i | VR_i\} \right\} \quad \text{equation (6)}$$

Next, the intersection of $SV_1$ and $EV_1$ with the skeletal pixels $SVR_i$ is determined and is defined as the SV Horizontal Limit Start $svHS_1$, EV Horizontal Limit Start $evHS_1$, SV Horizontal Limit End $svHE_1$, EV Horizontal Limit End $evHE_1$. The skeletal pixels between $svHS_1$ and $evHS_1$ define one horizontal portion of the skeleton and the skeletal pixels between $svHE_1$ and $evHE_1$ define a second horizontal portion of the skeleton.

With references to FIGS. 9A and 9B, the vertical portion of the skeleton of a Type 1 Cluster is determined with horizontal skeletonization. For horizontal skeletonization, horizontal rays $HR_j$ are casted and the ray hits $RH_{i,j}$ are recording according to equation 7:

$$PHR_j = \bigcup_{i=0}^{rows} (i|HR_j|RH_{i,j}) \quad \text{equation (7)}$$

where $PHR_j$ is a set of ray hits on ray $HR_j$. From the ray hits $PHR_j$, the skeletal pixels $SHR_j$ are determined according to equation 8:

$$SHR_j = \bigcup_{a=0}^{1} \left\{ \frac{PHR_{j,2a+1} + PHR_{j,2a+2}}{2} \middle| i, \frac{PHR_{j,2a+1} + PHR_{j,2a+2}}{2} \in F \right\} \quad \text{equation (8)}$$

and $SHR_j$ represents the pixel locations of the skeleton along ray $HR_j$. Each skeletal pixel is equidistant between two corresponding hits on a horizontal ray. Once the skeletal pixels are obtained, the start horizontal ray $SH_1$ and end horizontal ray $EH_1$ are defined as the first and last $HR_j$'s according to equation 9:

$$\{SH_1, EH_1\} = \left\{ \min_{1 \leq i \leq rows} \{i | HR_j\}, \max_{1 \leq i \leq rows} \{i | HR_j\} \right\} \quad \text{equation (9)}$$

Next, the intersection of $SH_1$ and $EH_1$ with the skeletal pixels $SHR_j$ is determined and is defined as the SH Vertical Limit Start $shVS_1$, EH Vertical Limit Start $ehVS_1$, SH Vertical Limit End $shVE_1$, EH Vertical Limit End $ehVE_1$. The skeletal pixels between $shVS_1$ and $shVE_1$ define one horizontal portion of the skeleton and the skeletal pixels between $ehVS_1$ and $ehVE_1$ define a second horizontal portion of the skeleton.

FIG. 10A illustrates the results after vertical and horizontal skeletonization of a Type 1 Cluster which is the union of all skeletal pixels between $SV_1$ and $EV_1$ and the skeletal pixels between $SH_1$ and $EH_1$. FIG. 10A also illustrates that portions of the skeleton are missing after these skeletonization steps. More specifically, the portions between $shVS_1$ and $svHS_1$, $evHS_1$ and $ehVS_1$, and finally the portions between $ehVE_1$ and $evHE_1$ are missing. With reference to FIG. 10B, To fill in the missing pixels a line between $shVS_1$ and $svHS_1$, is created and all skeletal pixels that are less than 1 pixel distance away from the line joining $shVS_1$ and $svHS_1$ are recorded. This process is repeated to fill in the skeletal pixels between $evHS_1$ & $ehVS_1$ and $ehVE_1$ and $evHE_1$.

Figure 11D:
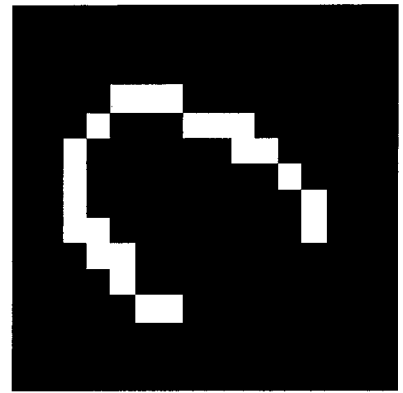
Figure 11C:
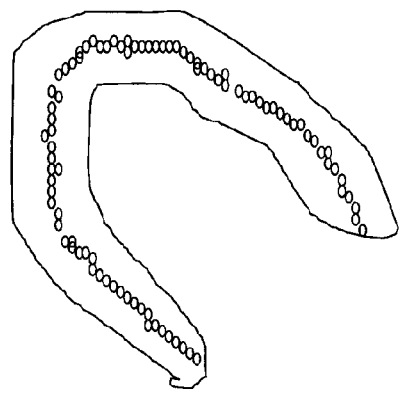
Figure 11B:
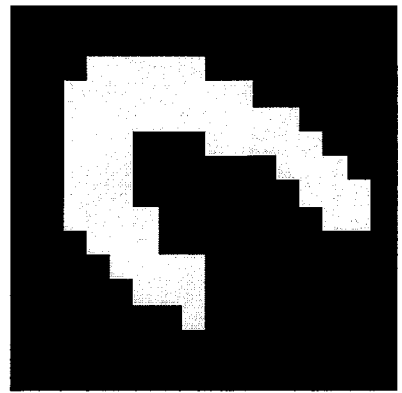

FIGS. 11A-11D illustrated the skeletonization process for the Type 1 Clusters. An identified Type 1 mask, shown in FIG. 11B, is skeletonized vertically S500 and horizontally S502. The missing skeletal are filled in S504 and the results are shown in FIGS. 11C and 11D.

Figure 13C:
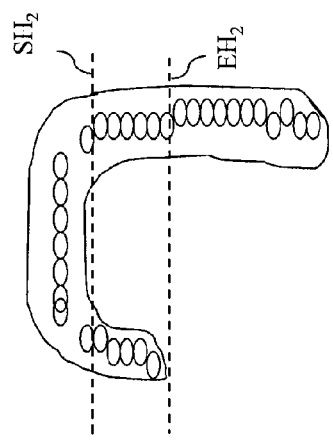
Figure 13D:
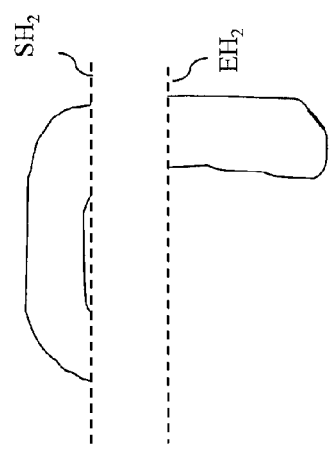
Figure 13A:
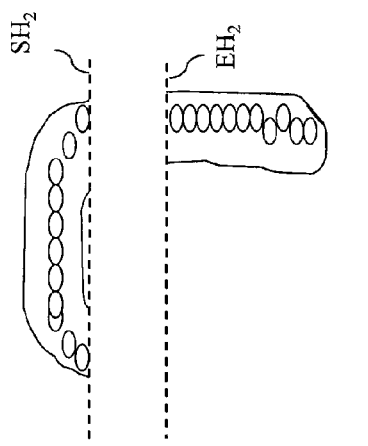
Figure 13B:
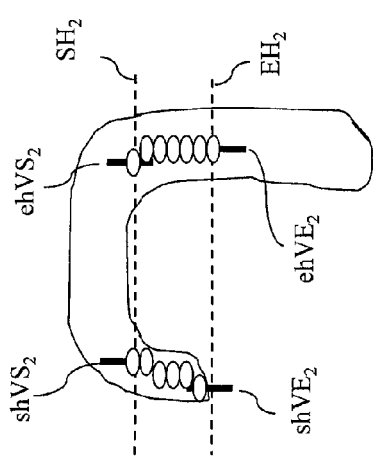

With reference to FIGS. 12A and 12B, Type 2 Clusters are defined as having only horizontal rays $HR_j$'s and no vertical ray $VR_i$'s, i.e. $HR_j>0$ and $VR_i=0$. To determine the skeleton S406 of a Type 2 Cluster a horizontal skeletonization S600, such as that described in S502 and FIGS. 9A and 9B, is followed by a classification of the remaining mask to determine the correct skeletonization to be performed. After skeletonization S600, the $SH_2$ and $EH_2$ are determined along $shVS_2$, $ehVS_2$, $shVE_2$, and $ehVE_2$ and the corresponding skeletal pixels as shown in FIG. 13A. The remaining mass is masked with the $HR_j$'s S602 as shown in FIG. 13B and those remain portions are classified and skeletonized S604 as shown in FIG. 13C. The skeletons from S600 and S604 are combined and then cleaned S606 to yield a final skeletonized Type 2 cluster shape shown in FIG. 13D.

FIG. 12B details the steps for determining the class for the remaining mass above $SH_2$ and below $EH_2$. After masking the myocardial mask with the horizontal rays, two segments are left S608 and either horizontal or vertical skeletonization, as previously described, can be use to determine the skeleton for the remaining masses. The classification is based on the pixel strength above $SH_2-1$ and below $EH_2+1$. If the non-zero pixel count is greater than 25 mm in the respective direction, then that respective skeletonization is used. After locating the $SH_2-1$ and $EH_2+1$ S610 as shown in FIG. 14A, the pixel count in both the $SH_2-1$ and $EH_2+1$ directions and determined S612. For example, if the pixel count in the ray direction $SH_2-1$ and $EH_2+1$ is greater than 25 mm, then vertical skeletonization is used such as in the upper most mass of the FIG. 14B. FIGS. 14B-14E demonstrate several embodiments of skeletonizing the remaining mass. FIG. 14B shows vertical skeletonization in both the upper and the lower mass. FIG. 14C shows horizontal skeletonization in both the upper and lower mass. FIG. 14D shows horizontal skeletonization in the upper mass and vertical skeletonization in the lower mass. FIG. 14E shows vertical skeletonization in the upper mass and horizontal skeletonization in the lower mass. FIG. 14E illustrates the properly classified and skeletonized remaining masses in which the upper most mass skeleton was determined with vertical skeletonization while the lower most mass skeleton was determined with horizontal skeletonization. In other masses, no skeletonization is also appropriate. Thus, based on the pixel count vertical skeletonization, horizontal skeletonization, and no skeletonization is performed on identified remaining masses.

Figure 15D:
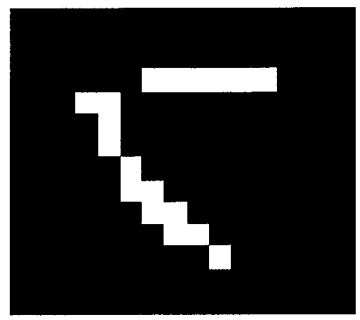
Figure 15C:
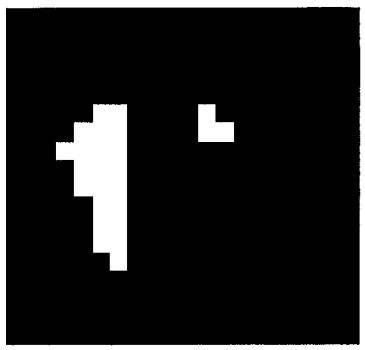
Figure 15B:
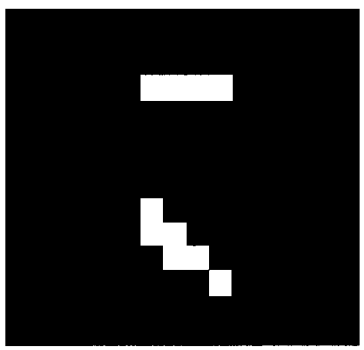
Figure 15A:
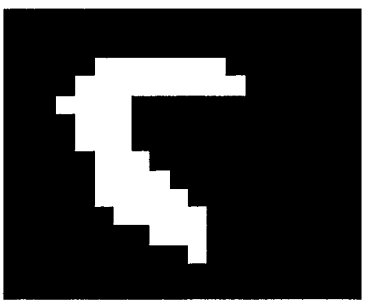

FIGS. 15A-15D illustrate the method steps described in FIGS. 12A and 12B. The skeletonization processor 66 receives and classifies the Type 2 mask illustrated in FIG. 15A. After horizontal skeletonization S600, the skeleton between $SH_2$ and $EH_2$ is determined, as shown in FIG. 15B, and the skeletonized mass is masked out S602 leaving the remaining mass above $SH_2$ and below $EH_2$ to be classified and skeletonized S604, as shown in FIG. 15C. The skeletons from steps S600 and S606 are cleaned S608 based on the $shVS_1$, $ehVS_1$, $shVE_1$, and $ehVE_1$ shown in FIG. 13A. The results of skeletonization of a Type 2 cluster is illustrated in FIG. 15D.

Figure 18A:
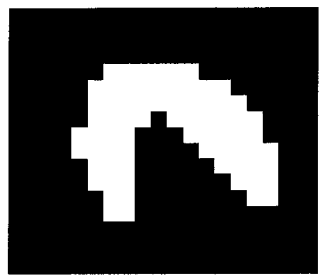
Figure 18B:
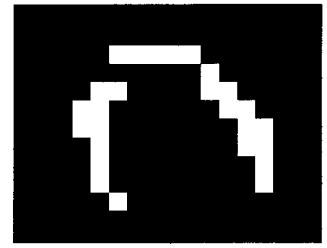
Figure 17A:
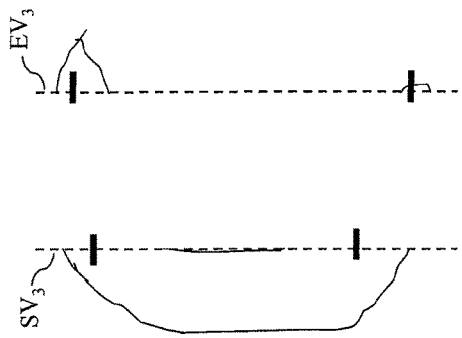
Figure 17B:
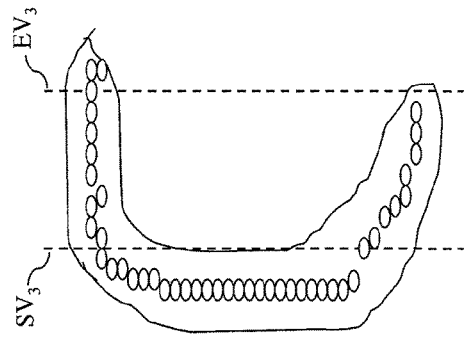
Figure 17C:
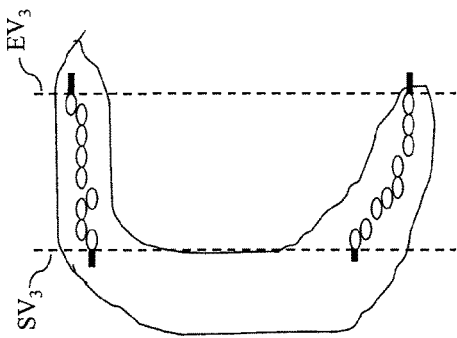
Figure 17D:
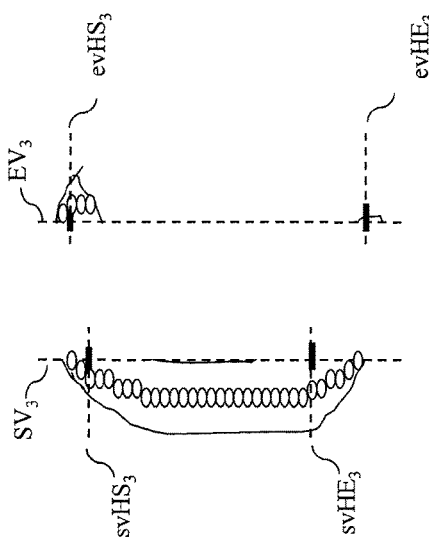

With reference to FIGS. 16 and 17A-17D, Type 3 clusters are defined has are defined as having only vertical ray $VR_i$'s and no horizontal rays $HR_j$'s, i.e. $VR_i>0$ and $HR_j=0$. To determine a Type 3 cluster S408, vertical skeletonization is performed S700 as shown in FIG. 17A. The skeletonized mass is masked out S702 based on the vertical rays $SV_3$ and $EV_3$, as shown in FIG. 17B. Horizontal skeletonization is then performed S704 on the remaining mass as shown in FIG. 17C. The horizontal limits, $svHS_3$, $evHS_3$, $svHE_3$, and $evHE_3$, of the vertical rays $SV_3$ and $EV_3$ are determined S706 and the skeletons from the vertical skeletonization steps S700 and horizontal skeletonization steps S704 are cleaned S708 based on the determined horizontal limits as shown in FIG. 17D. FIG. 18A illustrates a Type 3 cluster mask and FIG. 18A illustrates the resulting skeletonization.

Figure 19C:
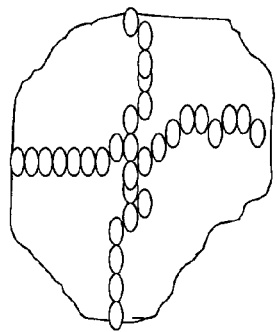
Figure 19E:
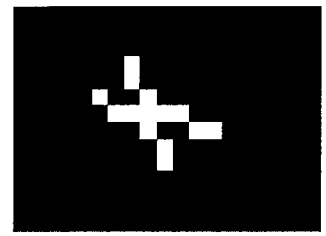
Figure 19B:
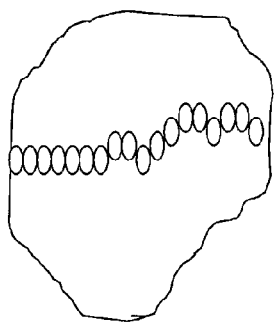
Figure 19D:
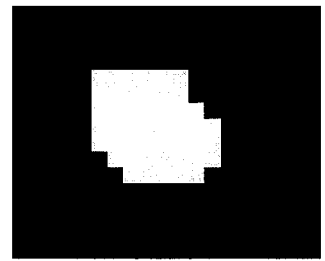
Figure 19A:
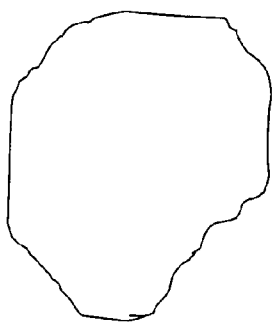

With reference to FIGS. 19A-19E, the Type 4 clusters are defined has having no vertical and no horizontal ray hits, $VR_i=0$ and $HR_j=0$. This is the simplest to skeletonized as no start vertical SV, end vertical EV, start horizontal SH, and end horizontal EH and their corresponding limits (svHS, evHS, svHE, evHE, shVS, ehVS, shVE, and ehVE) have to be located. For Type 4 clusters, a $VR_i$ and $HR_j$ are now defined according to equations 7 and 8:

$$VR_i = \begin{cases} \text{true}, & 2 \leq \sum_{j=0}^{columns} RH_{i,j} \\ \text{false}, & \text{otherwise} \end{cases} \quad \text{equation (2)}$$

$$HR_j = \begin{cases} \text{true}, & 2 \leq \sum_{i=0}^{rows} RH_{i,j} \\ \text{false}, & \text{otherwise} \end{cases} \quad \text{equation (3)}$$

where a ray is now defined as intersecting only 2 pixels. To determine the skeleton for a Type 4 cluster S410, vertical skeletonization, as shown in FIG. 19B, is followed by horizontal skeletonization for a final results shown in FIG. 19C. FIG. 19D illustrates the Type 4 binary mask while FIG. 19E illustrates the result after skeletonization.

With returning reference to FIG. 5, after the 2D skeletons for the various types are determined, they are stacked S412 to generate a three-dimensional (3D) skeleton of the L.V. Before the skeletal pruning S414 can be performed, the center-of-mass of the myocardial mass is determined based on the blood pool segmentation S106. Blood pool segmentation is critical for accurate COM computation and the ellipsoid fitting step S416 from which an accurate azimuth and elevation angle can be determined.

Figure 21A:
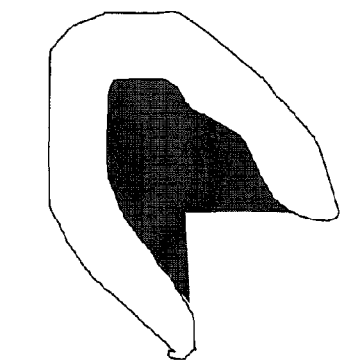
Figure 21B:
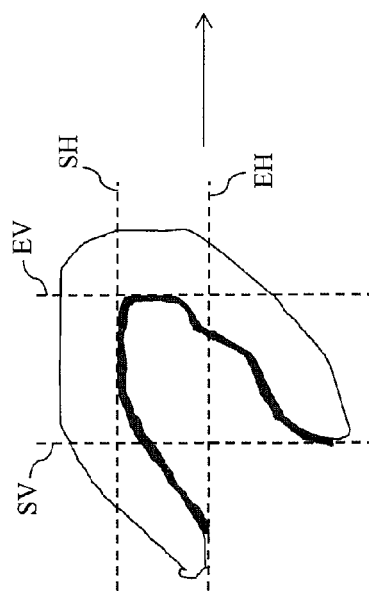
Figure 21C:
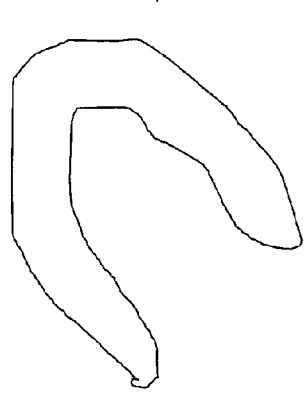
Figure 21D:
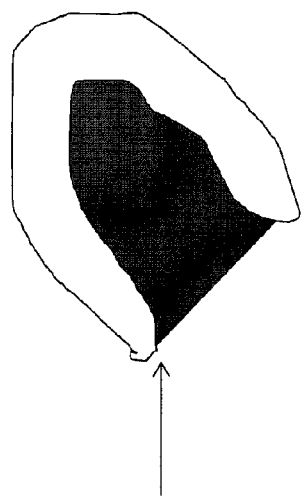
Figure 2E:
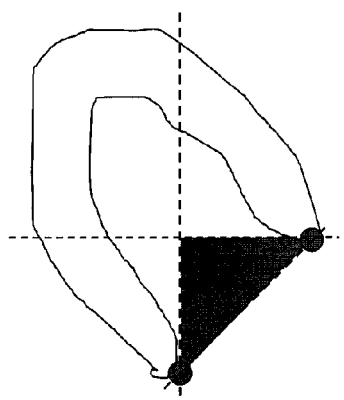
Figure 21F:
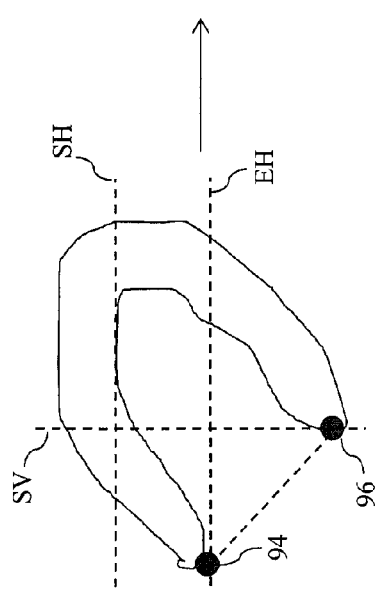

With reference to FIGS. 20 and 21A-21F, the blood pool processor 68 determines the blood pool COM for each optimized binary mask of the L.V. transverse volume based on a blood pool segmentation algorithm 92. From the optimized myocardial mask S104, slices with at least one $VR_i$ and $HR_j$ are located S800, FIG. 21A. Among these slices, the SV and EH are determined S802. To locate the blood pool within the apex of the L.V., the points corresponding to the endocardium are determine and stored S804, FIG. 21B, and the all the pixels between the endocardium are filled and labeled blood pool pixels S806 as shown in FIG. 21C. To determine the blood pool at the base of the L.V. the a point on the epicardium near the aortic valve 94, e.g. the posterior aortic root, and a point on the epicardium near the mitral valve 96, e.g. the atrioventricular root, are located and labeled S808 and S810, FIG. 21D. A line is used to join these points S812 and all pixels less than 7 mm in distance from within the endocardium is labeled as blood pool pixels S814, FIG. 21E. All of the blood pool pixels are combined into a single composite blood pool S816, FIG. 21F, and thresholded according to a preselected threshold. If the number of pixels in the blood pool is less than this threshold, the process is iterated to adjust the center of the blood pool to to improve accuracy. Significant decreases in the count of blood pool pixels may symbolize a bad quality image, a case with heavy perfusion defects, and/or a projection with high intensity pixels in other organs, such as the liver or abdomen.

For myocardial masks which have either a $VR_i$'s or $HR_j$'s missing, such as Type 2, 3 and 4 clusters, the blood pool processor 68 determines the blood pool and COM according to the algorithm 98 and/or 100. With reference to FIGS. 22A and 22B, for myocardial binary masks with $VR_i=0$ horizontal ray are used to locate the blood pool pixels between the located endocardium points S900 and the located points 94, 96 at the base of L.V. S902. The blood pool between SH and EH is labeled S904. To fill and label the blood pool between points 94 and 96, horizontal rays are casted S906 from EH+1 until the point close to the mitral valve 96 is estimated as the first non-zero pixel along the last ray casted with presence of non-zero pixels, as shown in FIG. 22B. The labeled blood pool pixels are composited and thresholded S908 according to a preselected threshold to form the blood pool for the corresponding binary mask as shown in FIG. 22B. If the number of pixels in the blood pool is less than this threshold, the process is iterated to adjust the center of the blood pool to improve accuracy. Significant decreases in the count of blood pool pixels may symbolize a bad quality image, a case with heavy perfusion defects, and/or a projection with high intensity pixels in other organs, such as the liver or abdomen.

With reference to FIGS. 23A and 23B, for myocardial binary masks with $HR_j=0$ vertical ray are used to locate the blood pool pixels between the located endocardium points S1000 and the located points 94, 96 at the base of L.V. S1002. The blood pool between SV and EV is labeled S1004. To fill and label the blood pool between points 94 and 96, vertical rays are casted S1006 from SV-1 until a pixel close to the aortic valve 94 is estimated as the last non-zero pixel along the last ray with presence of a non-zero pixels, as shown in FIG. 22B. The labeled blood pool pixels are composited and thresholded S1008 to form the blood pool for the corresponding binary mask as shown in FIG. 23B. If the number of pixels in the blood pool is less than this threshold, the process is iterated to adjust the center of the blood pool to improve accuracy. Significant decreases in the count of blood pool pixels may symbolize a bad quality image, a case with heavy perfusion defects, and/or a projection with high intensity pixels in other organs, such as the liver or abdomen.

With reference to FIG. 23, a myocardial mask (top row) is illustrated with its corresponding segmented blood pool (bottom row). After the blood pool for the optimized mask S106 is determined, the COM processor 70 determines x,y coordinate for the center-of-mass for each blood pool slice based on non-zero pixel location of the blood pool. The z coordinate is determined based on the extents of the optimized myocardial mask as the extents of the blood pool may not represent the tru extent of the myocardium in the z direction.

With returning reference to FIG. 5, after computing the COM of the L.V., with the x,y coordinate of the COM for each optimized mask slice, the skeletonization processor 66 can resume the skeletonization method 84 with the skeletal pruning S414 step to removed extraneous skeletal pixels or pixels leaking at the L.V. boundaries. The leaking of skeletal pixels can be caused by the thickness of the myocardial masks at certain locations. To prune the skeletons from step S412 the skeletonization processor performs a distance transform and a distance binning algorithm 102. With references to FIGS. 25 and 26, the COM and skeleton are used to determine the Euclidian distance of each non-zero pixel from the COM S1100. The skeletal pixels are then binned S1102 according to their maximum and minimum distance observed in the previous step S1100 into several intervals of distances. A histogram 104 is generated S1104 based on the distance bins from S1102 and the number of pixels which falls into each corresponding bin. From the histogram 104, several attributes of the histogram are determined to prune the skeleton such that pixels outside of preselected thresholds are designated as background pixels. After the histogram peak 106 is located S1106 which refers to the maximum frequency point, the predetermined boundary conditions S1108 of the histogram are used to determine the upper and lower bin thresholds S1110 and the upper and lower frequency threshold S1112 on either side of the maximum peak 106. The skeleton is pruned S1114 to remove the pixels outside the determined thresholds S1110 and S1120.

With returning reference to FIG. 5, with the pruned skeleton from step S1114, the COM processor fits an ellipsoid S416 to the pruned or optimized 3D skeleton from S1114 and determines the center of mass in the z-direction of the ellipsoid. The parameterization processor 72 determines the pose, e.g. azimuth angle and elevation angle, of the left ventricle based on the fitted ellipsoid. The parameterization processor 72 determines various parameters of the left ventricle, e.g. blood flow, regional myocardial blood flow, flow reserve, ejection fraction, and the like, based on the azimuth angle, elevation angle, z-direction COM, x,y-direction COM, the fitted ellipsoid, the segmented blood pool masks, the optimized myocardial masks, and/or the skeleton which all can be output to the display unit 48 of the graphical user interface 46 for inspection by a clinician along with 2D/3D projection images of the myocardium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for cardiac imaging, comprising:
reconstructing functional imaging data of a subject into a diagnostic image including at least a myocardium;
determining the pose and geometry of the myocardium in the diagnostic image, wherein determining the pose and geometry of the myocardium includes:
segmenting a left ventricle in the diagnostic image,
generating a left ventricle myocardial mask,
computing a center of mass of the left ventricle in the diagnostic image,
skeletonizing the left ventricle myocardial mask to generate a myocardial skeleton,
pruning the myocardial skeleton,
estimating diagnostic parameters of the myocardium based on the determined pose and geometry;
displaying at least a portion of the diagnostic image including the myocardium on a display device.

2. The method according to claim 1, wherein pruning the myocardial skeleton includes:
calculating a distance from each non-zero skeletal pixel to the center of mass of the left ventricle;
binning the calculated distances into distance bins;

generating a histogram from a number of pixels in each of the distance bins;
determining from the histogram a lower bin threshold, an upper bin threshold, a low bin frequency threshold, and an upper bin frequency threshold;
removing from the skeleton pixels outside of the lower and upper bin thresholds and the lower and upper bin frequency thresholds.

3. The method according to claim 1, further including:
correcting the left ventricle mask for boundary thickening and myocardial gaps.

4. The method according to claim 1, further including:
segmenting the left ventricle mask to generate a stack of left ventricle mask slices;
locating a top and a bottom of the stack;
locating an upper most mask slice of the stack and a lower most mask slice of the stack with a closed or semi-closed cavity;
masking the upper most mask slice of the stack with a second to upper most mask slice of the stack;
masking the lower most mask slice of the stack with a second to lower most mask slice of the stack; and
filling between the upper most and lower most slices.

5. The method according to claim 1, further including for heavily perfused cases:
segmenting the left ventricle mask into mask slices;
locating upper and lower most mask slices with a myocardial gap using ray casting to locate cavities;
applying a slice filling algorithm to fill between the upper and lower most mask slices.

6. The method according to claim 1, wherein skeletonizing includes:
segmenting the left ventricle mask into mask slices;
clustering the mask slices using ventricle and horizontal ray casting to form a plurality of clusters for each slice;
defining a blood pool from the clusters.

7. The method according to claim 6, wherein clustering the mask slices includes one or more of:
for each slice, casting vertical rays to define ray hits and horizontal limits of the myocardium and casting horizontal rays to define ray hits and vertical limits of the myocardium cavity and filling portions of the myocardium beyond the horizontal and vertical limits;
masking each mask slice to remove portions between the vertical limits, classifying strengths of pixels above the upper vertical limit and below the lower vertical limit based on strengths of pixels immediately adjacent the vertical limits, combining the classified pixels above the upper and below the lower vertical limits with pixels between the vertical limits to define a cleaned skeleton;
masking each mask slice to remove portions between the horizontal limits, classifying strengths of pixels above the left horizontal limit and below the right horizontal limit based on strengths of pixels immediately adjacent the horizontal limits, combining the classified pixels above the left and below the right horizontal limits with pixels between the horizontal limits to define a cleaned skeleton.

8. The method according to claim 1, further including:
identifying slices of the myocardial mask which have at least one horizontal or vertical ray;
identify an edge and point of each horizontal ray close to an aortic valve;
identify an edge and point of each vertical ray close to a mitral valve, the edge end points of the horizontal and vertical rays defining a line;
labeling pixels less than a preselected distance, e.g., 7 mm, from the line as blood pool pixels.

9. The method according to claim 1, further including:
identifying slices of the myocardial mask which have at least one horizontal or vertical ray;
identifying points on the myocardial mask intersected by at least one of the rays;
fill in pixels between the identified points as blood pool pixels.

10. One or more computer processors programmed to perform the method according to claim 1.

11. A non-transitory computer readable medium carrying software which controls one or more processors to perform the method of claim 1.

12. A cardiac imaging system comprising:
a diagnostic scanner configured to generate the functional imaging data of the subject;
one or more processors configured to perform the method according to claim 1; and
a display configured to display the diagnostic image and the diagnostic parameters of the myocardium.

13. A cardiac imaging apparatus comprising:
a diagnostic scanner configured to acquire functional image data of a subject, the functional imaging data including at least myocardium data;
a video display;
one or more computer processors configured to:
reconstruct a functional diagnostic image of a left ventricle of a subject from the functional image data,
segment the left ventricle of the subject in the reconstructed functional image,
generate a left ventricle myocardial mask,
determine a center of mass of the left ventricle in the reconstructed functional image,
skeletonize the left ventricle myocardial mask to generate a myocardial skeleton,
determine a distance from each non-zero skeletal pixel of the reconstructed diagnostic image to the center of mass of the left ventricle,
bin the calculated distances into distance bins,
generate a histogram from a number of pixels of the reconstructed diagnostic image in each of the distance bins,
determine from the histogram a lower bin threshold, an upper bin threshold, a lower bin frequency threshold, and an upper bin frequency threshold,
remove skeletal pixels of the reconstructed diagnostic image outside of the lower and upper bin thresholds and the lower and upper bin frequency thresholds, and
control the video display to display at least the myocardium of the diagnostic image with the skeletal pixels outside of the lower and upper bin thresholds and the lower and upper bin frequency thresholds removed.

14. The apparatus according to claim 13, wherein the one or more computer processors is further configured to:
segment the left ventricle mask to generate a stack of mask slices;
locate an upper most mask slice of the stack and a lower most mask slice of the stack that have a closed or semi closed cavity;
mask the upper most slice of the stack with a second to upper most mask slice and mask the lower most slice of the stack with a second to lower most mask slice of the stack;

fill between the upper most and lower most slices to define a blood pool; and wherein the displayed diagnostic image further includes a depiction of the blood pool.

15. A cardiac imaging apparatus comprising:

a display device;

one or more processors programmed to:
reconstruct a diagnostic image of at least a left ventricle of a subject from functional imaging data generated by a diagnostic scanner,
segment the left ventricle in the diagnostic image of the subject,
generate a left ventricle myocardial mask,
determine a center of mass of the left ventricle,
segment the left ventricle mask into mask slices,
cluster the mask slices using vertical and horizontal rays to cast a plurality of clusters for each slice,
define a blood pool from the clusters, and
control the display device to display at least the myocardium of the diagnostic image.

16. The apparatus according to claim 15, wherein the one or more processors is further programmed to cluster the mask slices by:
for each slice, casting vertical rays to define ray hits and horizontal limits of a myocardium cavity containing at least a portion of the blood pool and casting horizontal rays to define ray hits and vertical limits of the myocardium cavity,
filling portions of the myocardium cavity beyond the horizontal and vertical limits,
masking each mask slice to remove portions between the vertical limits,
classifying pixels of the diagnostic image above the upper vertical limit and below the lower vertical limit based on pixels immediately adjacent the vertical limits,
combining the classified pixels above the upper and below the lower vertical limits with pixels between the vertical limits to define a myocardial skeleton,
masking each mask slice to remove portions between the horizontal limits,
classifying the pixels to the left of the left vertical limit and to the right of the right vertical limit based on the pixels immediately adjacent the horizontal limits,
combining the classified pixels to the left and right of the horizontal vertical limits with pixels between the horizontal limits to define a cleaned myocardial skeleton,
wherein the displayed diagnostic image includes the cleaned myocardial skeleton.

17. The cardiac imaging apparatus according to claim 15, wherein the one or more processors is further programmed to:
generate a stack of mask slices;
locate an upper most mask slice of the stack and a lower most mask slice of the stack with a closed or semi closed cavity;
masking the upper most slice of the stack with a second to upper most mask slice and masking a lower most slice of the stack with a second to lower most mask slice of the stack; and
filling between the upper most and lower most slices to define the blood pool in the myocardium cavity.

18. The cardiac imaging apparatus according to claim 15, further including a diagnostic scanner configured to generate the functional imaging data which the one or more processors are configured to reconstruct into the diagnostic image.

* * * * *